United States Patent
Betts-Lacroix et al.

(10) Patent No.: US 10,463,017 B2
(45) Date of Patent: Nov. 5, 2019

(54) DEVICE AND METHOD FOR MULTI-DIMENSIONAL CLASSIFICATION OF RODENT VOCALIZATIONS

(71) Applicant: Vium Inc, San Mateo, CA (US)

(72) Inventors: Jonathan Betts-Lacroix, Belmont, CA (US); Laura Schaevitz, Los Gatos, CA (US)

(73) Assignee: Vium Inc., San Mateo, CA (US)

( * ) Notice: Subject to any disclaimer, the term of this patent is extended or adjusted under 35 U.S.C. 154(b) by 278 days.

(21) Appl. No.: 15/667,862

(22) Filed: Aug. 3, 2017

(65) Prior Publication Data

US 2019/0037801 A1    Feb. 7, 2019

(51) Int. Cl.

| | |
|---|---|
| *A01K 1/03* | (2006.01) |
| *A01K 29/00* | (2006.01) |
| *A61B 5/00* | (2006.01) |
| *A61B 5/16* | (2006.01) |
| *A61B 5/11* | (2006.01) |
| *G16H 50/00* | (2018.01) |

(52) U.S. Cl.
CPC ............ *A01K 1/031* (2013.01); *A01K 29/005* (2013.01); *A61B 5/1105* (2013.01); *A61B 5/1128* (2013.01); *A61B 5/165* (2013.01); *A61B 5/4064* (2013.01); *A61B 5/4803* (2013.01); *A61B 5/7246* (2013.01); *A61B 5/7264* (2013.01); *A61B 5/1123* (2013.01); *A61B 2503/40* (2013.01); *A61B 2562/0204* (2013.01); *G16H 50/00* (2018.01)

(58) Field of Classification Search
CPC .......................... A01K 1/031; G06K 9/00335
USPC ....................................... 340/573.1
See application file for complete search history.

(56) References Cited

U.S. PATENT DOCUMENTS

| | | | |
|---|---|---|---|
| 2008/0306980 A1* | 12/2008 | Brunner | A01K 1/031 |
| 2010/0111359 A1* | 5/2010 | Bai | A01K 29/005 |
| | | | 382/103 |
| 2011/0082574 A1* | 4/2011 | Pachet | A01K 15/02 |
| | | | 700/94 |

* cited by examiner

*Primary Examiner* — Fabricio R Murillo Garcia
(74) *Attorney, Agent, or Firm* — Kim Rubin

(57) ABSTRACT

The field of this invention is classifying animal behaviors. In particular the fields of this invention include using animals in vivariums, such as rodents, particularly mice. In a vivarium cage, animals create ultrasonic vocalizations. In addition, their phenotype changes over time. The vocalizations, a current phenotype, and the cage environments are inputs to a multi-dimensional classifier using clustering algorithms to find multi-dimensional close relationships. Such close relationships may be identified as particular behavior.

8 Claims, 14 Drawing Sheets

Fig. 13

Animals Requested

| Species | Strain | Category | Qty | Age | Weight | Gender | Description |
|---|---|---|---|---|---|---|---|
| Mouse | C57Bl/6 | D | 55 | 6 weeks | | Male | |

Treatment Groups

| ID | Treatment Group Name | Qty | Test Material | Dose Volume and Route | Notes | Animal IDs |
|---|---|---|---|---|---|---|
| 1 | MFB | 5 | 1x 10^5 GL261 | Medial forebrain bundle | | |
| 1 | D.Striatum | 5 | 1x 10^5 GL261 | Dorsal striatum | GBM Evidence | |
| 1 | MCtx | 5 | 1x 10^5 GL261 | Motor cortex | | |
| 1 | GP | 5 | 1x 10^5 GL261 | Globus Pallidus | | |
| 1 | CB | 5 | 1x 10^5 GL261 | Cerebellum | GBM Evidence | |
| 1 | SN | 5 | GL261 | Substantia Nigra | No evidence | |
| 1 | VTA | 5 | GL261 | Ventral tagmental area | | |
| 1 | NAc | 5 | GL261 | Nucleus Accumbens (shell) | | |
| 1 | SC | 5 | 1x 10^5 GL261 | Superior colliculus (motor) | GBM Evidence | |
| 1 | Hypothalamus + SCN | 5 | GL261 | Super ciasmatic nucleus | | |
| 1 | RN | 5 | GL261 | Red Nucleus | No evidence | |

Fig. 14

Procedure Schedule

| Day | Date | Task | Description | Assigned To |
|---|---|---|---|---|
| -7 | | Baseline Monitoring | Mousera App including motion (circadian and activity levels), respiratory, & weight | |
| 0 | | Intracranial implantation of GL261 cells | Sterile stereotaxic implantation of 1 x 10^5 GL261 cells at one of 11 coordinates (Groups) | |
| 0 - 49 | | Continuous Monitoring | Mousera App including motion (circadian and activity levels), respiratory, & weight | |
| Terminal endpoint | | Euthanize/perfuse brains for histology | Animals will be perfused and brains removed for H&E staining to assess size and location of tumors. | |

DEVICE AND METHOD FOR MULTI-DIMENSIONAL CLASSIFICATION OF RODENT VOCALIZATIONS

BACKGROUND OF THE INVENTION

The field of this invention is classification of rodent vocalizations. One embodiment automatically examines many vocalizations and identifies common patterns. Another embodiment automatically associates vocalizations with known body behaviors. Yet another embodiment automatically associates vocalizations as either "positive" or "negative." Yet another embodiment automatically associates vocalizations with previously known phenotypes, such as disease-positive or disease-negative behaviors. Yet another embodiment automatically associates vocalizations as occurring prior to, with, or after known body behaviors, generating behavioral "phrases." Yet another embodiment combines vocalization with other observed and known behaviors to identify, classify or correlate behaviors based on merged vocalizations and visual behaviors. Yet another embodiment associates vocalizations, optionally combined with other behaviors, to identify cognitive, emotional, or other "thinking" states of rodents.

An environment for embodiments is typically a vivarium with rodents in cages, where cages are equipped with individual audio—usually ultrasonic—sensors and vision sensors such as cameras. Other sensors may be used, such as temperature, air chemistry, animal scales, RFID, and the like. A vision system may identify other animal phenotype elements, such a respiration rate, respiration quality, heart rate, and other stand-alone behaviors, behavioral phrases, or longer-term behaviors.

Both mice and rates generate frequent and complex vocalizations, often in the ultrasonic range, such as around 22 KHz or 50 KHz.

Understanding vocalizations and their relationship to known or new behaviors adds significantly the value of vivarium-based studies such as drug efficacy, and characterization of animal types.

Continuous data recording of both ultrasonic vocalizations and vision-based activity, in an animals' home cage, with subsequent automated multi-dimensional analysis of both data types, provides improvement over the prior art.

SUMMARY OF THE INVENTION

Descriptions, lists and examples herein, and in Figures, are non-limiting unless otherwise so stated.

Cages in a vivarium house animals, such as mice or rats. Each cage is equipped with a full-time ultra-sonic audio sensor and a full-time video camera. The cages are "home cages," so that animals do not need to be disturbed from their natural environment, including their natural nocturnal behavior, for data collection. Data from these sensors is analyzed automatically by algorithms executed on a computer, which may be local or connected remotely via a network. Such analysis may be performed in real time, or, data may be recorded and then analyzed at a later time.

Such continuous data collection in an animal's natural environment provides for more accurate and comprehensive analysis than periodic monitoring, monitoring only in special cages, or monitoring by human observation.

Sensors may include, non-limiting, ultrasonic microphones, microphones response in a human audible range, black-and-white or color video cameras, infrared cameras, thermal cameras, still cameras, motion detectors, thermometers, animal scales, RFID sensors, exercise monitors, food or water sensors, urine sensors, chemical sensors and the like.

A first embodiment collects vocalization data for a given animal type and environment. An animal type may include a species, genetic profile, gender, age, health, any performed animal treatments, and the like. Environment may include other animals if any, temperature, food, bedding, lighting, scents, stimuli, and the like. The vocalizations are processed using a clustering algorithm to find individual "words" and a vocabulary of such words is created. Such words may be named, numbered or otherwise identified. The clustering algorithm also identifies the range of characteristics for each cluster for future classification of new vocalization into one of the words in the vocabulary. By analyzing sequences of words, "phrases" may be identified. Sequencing may include repeats, spacing (gaps between words), and generation of or prediction by state machines or automata models. Such analysis in the embodiment is independent of specific behaviors, but is identified with animal type and environment. It is useful to identify words or phrases that are the same for different animal types or environments, and also to identify words or phrases that differ with different animal types or environments. This embodiment may be performed stand-alone, or performed prior to other embodiments, or combined with other embodiments. Both methods and devices are claimed for these embodiments.

A second embodiment automatically classifies vocalizations as "positive" or "negative," creating a weight for each association, using correlation, clustering, and other statistical analysis methods. "Positive" and "negative" refer to known phenotypes, which may be primarily behavioral, such as known "happy" v. "unhappy" behaviors. Alternatively the positive and negative phenotypes may refer to health, disease or treatment. For example, a negative phenotype may refer to behaviors of a healthy animal while a positive phenotype refers to the behaviors of an animal with brain cancer. Such binary (actually, weighted) classification is common and useful to determine, for example, if an animal is sick or healthy. Such classification may also be used to determine more subtle characteristics, such as whether or not an animal is over jet lag from transport, or has adapted to a new cage-mate, or is satisfied with its husbandry.

For these embodiments, vocalizations are compared with known phenotypes (behaviors) associated with the desired characteristic.

A third embodiment creates weighted associations of vocalizations with video behaviors. For this embodiment, the video behaviors may or may not have already been classified. For example, a happy, healthy animal exploring its cage may emit vocalizations along with the exploring. When an animal is first socializing with a new cage mate, it may emit different vocalizations. "Video behaviors" refers to any behavior that is identifiable from video frames. Typically these embodiments create a table of at least 2-tuples where each 2-tuple comprises one vocalizations classification and one video behavior classification. A correlation or frequency metric may be included in each table line.

A fourth embodiment examines vocalizations between two animals in the same cage. This may be viewed as a "call" and "response," where the response of the second animal is responsive to the call of the first animal. Both the call and response comprise vocalizations. Such vocalization may be first categorized into known "words," or they may be processed by embodiments from raw audio data. The later case is useful if the existing vocabulary of words does not include vocalizations that may be unique to two animals communicating. Although such call and responses may be analyzed and categorized solely from audio data, it is particularly useful to compare the audio calls and responses with video behaviors, as video behaviors between two rodents are well studied. Typically, such an embodiments crates a table of at least 3-tuples, where each tuple comprises: a call and response vocalization pair, a corresponding video behavior (of one or both animals), and a correlation weight or frequency. Additional data may be added on each table line.

For the third and fourth embodiments summarized above, each table may be specific for a single animal type and single environment. However, it is useful to combine such a large number of tables into a smaller, more manageable number of tables (or a single table) by combining table lines that are similar from multiple tables, or otherwise merging tables, such by adding animal type or environment identification into table lines. Embodiments specifically include such table reduction.

A fifth embodiment considers vocalizations in the context of prior, during, or after known video behaviors. These embodiments may be for a single animal of for more than one animal. For non-limiting convenience in this summary, we consider a single animal. A prior vocalization may be, "I am going to do something." A during vocalization may be, "I am now doing something." An after vocalization may be, "I did something." One example is, "I am thirsty and will look for water." Another example is, "I am defending my territory and you should move away." A third example is, "I am exercising." A fourth example is, "I have just finished mating." As can be appreciated, the first example is valuable because it provides a prediction of future, but not yet observed, activity (drinking). The second example is valuable because it may be a vocalization indicating a social relationship that is not directly observable with video behavior, such as the second animal moving away with no fight occurring. The fourth example may be valuable because the mating may have been in a nest and not video observable at all.

A sixth embodiment considers vocalizations, video behaviors, and changes in phenotype in aggregate to associate the aggregate behavior with "what an animal is thinking." Examining only visible behaviors is nice, but often, for example, when testing psychoactive drugs, it is useful to know more directly if an animal is happy, angry, confused, in pain, and the like. The embodiment begins with a known set of cognitive, emotional, or innate states with known associated behaviors. These are used to build a library of identification, classification and correlation with the aggregate observed vocalizations, video behaviors, and other changes in phenotype. Then, observed aggregates may be used to deduce the one or more cognitive, emotional or innate states of the animal, or a likelihood of such one or more states.

See below for definitions.

BRIEF DESCRIPTION OF THE DRAWINGS

FIG. 13 An exemplary treatment plan for a study.
FIG. 14 An exemplary procedure schedule for a study.

DETAILED DESCRIPTION

Figure 1:
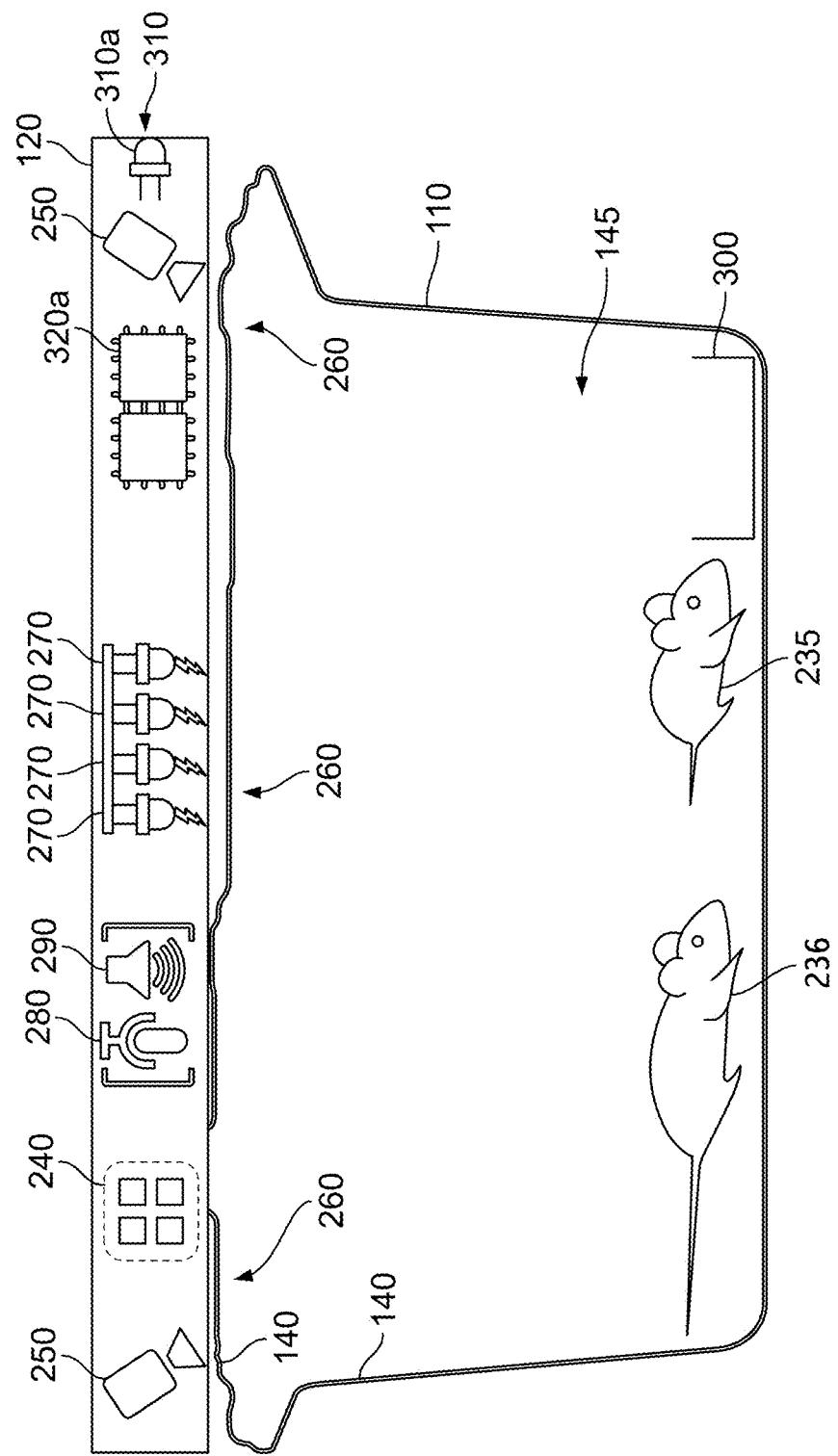
FIG. 1 Two mice in a cage with sensors in a vivarium.

Turning now to FIG. 1, we see a schematic side view of a cage with sensors. The periphery of the cage, often constructed from clear plastic, is shown as 110 and 140, for the outside and inside surfaces respectively. The interior of the cage, ideally sterile, per the definition of sterile in this specification, is 145. Thus the sterile border is between 140 and 110. A bedding area is shown 300. 260 shows in three places clear areas at the top of the cage through which cameras 250 may view the inside of the cage, and through which visible light and infrared light, from LEDs 270, may enter the cage. Cages may be disposable or sterilized between studies. Ideally, and key to some embodiments, is that there are no electrical penetrations of the cage periphery, 110 and 140. Cameras, which may be still or video, monochrome, color or infrared (IR), multiple or single, are shown 250. 280 and 290 show respectively a microphone and speaker, which may be used for either ambient (vivarium) or in-the-cage audio use. One or more microphones, such as 280, may include ultrasonic sensitivity, such as in the range of 14 to 100 KHz, or another range. It a preferred embodiment to particularly pick up ultrasonic animal vocalizations broadly around 22 KHz and 50 KHz. A microphone should be suitably placed, and a cage top may need to be adapted to permit vocalizations of animals in the cage to be readily picked up while minimizing picking up noise, including vocalizations from neighboring cages; air motion noise, and non-vocalization noise from the animals such as chewing, exercise, burrowing, and the like. In some embodiments, "low noise" bedding is used, along with "low noise" exercise equipment such as a climbing ladder in place of an exercise wheel. Another embodiment places a bearing in an exercise wheel to minimize mechanical noise from wheel motion.

240 shows exhaust air sensors, such as temperature, humidity, ammonia concentration, and the like. 320a shows local processing electronics, which may include CPU, analog and digital processing, including video image processing, audio compression, storage and communication, in any combination. 310a shows an LED pointing away from the cage, which may be used as an indicator for humans, such as the cage needs attention, or as an optical communications element. 310 shows a base, enclosure or "slab" that contains some or all of the electronics and sensors. Ideally this slab 310 is separate from the cage 110, so that cages may be easily removed, swapped, or replaced without disturbing the electronics, and similarly, all of the electronics in the slab 310 may easily be installed, serviced, updated, or swapped as slab units without disturbing the cage or its animals. A gasketed penetration, or a tiny penetration (0.1 to 5 mm, or 0.3 to 2 mm) may be used to pass ultrasonic vocalization from the cage to an ultrasonic microphone in, on, or proximal to the slag. Cages may slide in and out of their holding racks on rails, while the slap is mounted overhead each cage. Similarly, slabs may sit simply on supports, with electrical connection via a connector or fingers. In this way, both the electronics and the cages may be removed and replaced without disturbing the other. Other sensors may also or alternatively be used, as discussed below. Husbandry elements such as food, water and bedding are not shown. Also not shown in this Figure are supply and exhaust air ducting. These husbandry elements may also be monitored by the sensors in slab 310 or by sensors elsewhere.

Two animals are shown in FIG. 1 as 235 and 236. Here, there are two mice. As described above and below, embodiments may use a wide range of animals for studies. The identities of the two mice, 235 and 236, are distinguished in different embodiments by different sensors, such as RFID (not shown), barcodes on the animals (not shown) or video processing via cameras 250. These two mice, 235 and 236, may be observed via the sensors and electronics to generate two distinct phenotypes, as explained below.

Animals may receive either positive or negative feedback to encourage or discourage behavior. Such feedback mechanisms are not shown in FIG. 1, except for one speaker, 290, and LEDs, 270. Heat, such as from an incandescent source (not shown) or LEDs may be used to provide warmth as a positive reward, which may be directed at a single animal. Visible light, a strobe, or a sharp noise may be used as negative stimulus.

FIG. 1 is schematic only. Actual sensors and cage design may differ substantially from the shapes and locations shown.

In some embodiments and claims the term "phenotype" or "behavioral phenotype" may be used or substituted in place of "set of behaviors" or "behavior," and vice-versa. All such wording substitutions are specifically claimed.

Figure 2:
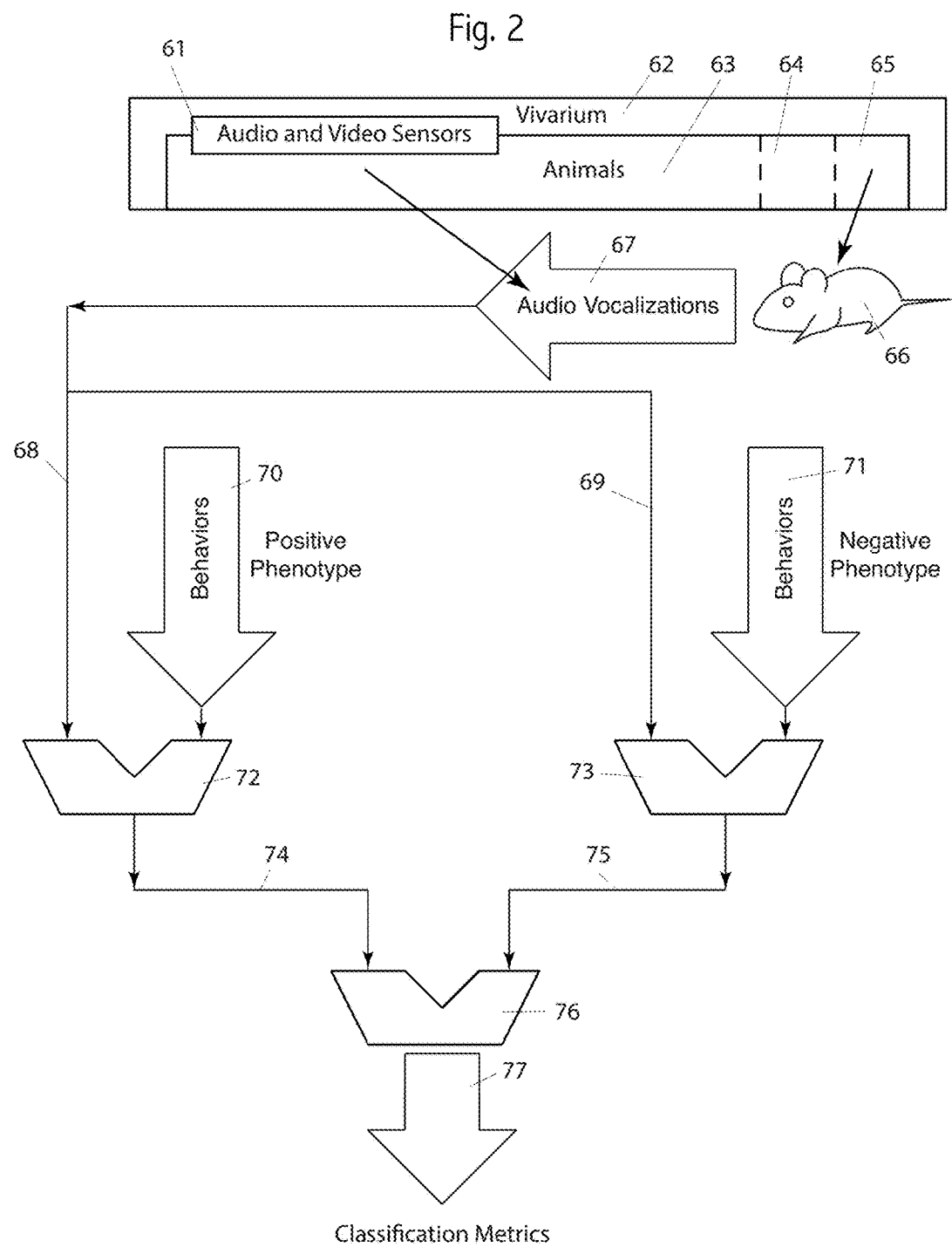
FIG. 2 A block diagram showing an embodiment of comparing rodent vocalizations against known positive and negative phenotypes for classification.

Turning now to FIG. 2, we see a block diagram of embodiments that classify and create metrics for rodent vocalizations as compared to known positive 70 and negative 71 phenotypes. Such positive and negative phenotypes are generally known in the art. They may be more accurately or comprehensively described, or bounded, limited, expanded, or quantified by embodiments herein.

A vivarium 62 comprises animals 63 in cages 64 and 65. Home cages have audio and video sensors 61 proximal to each cage. Mouse 66 is an exemplary animal, living in home cage 65. Embodiments include sensors not proximal to cages and animals not in home cages. Mouse 66 generates vocalizations 67, both human-audible and ultrasonic, as detected by audio sensors 61, and stored and communicated by hardware not shown in this Figure. (Conventional non-transitory memory devices, computers and microprocessors, and network and communication equipment may be used for these purposes.) Statistical and algorithmic comparators 72 and 73 provide comparisons respectively between the vocalizations 68 and 69 respectively and predetermined positive 70 and negative 71 phenotypes, respectively, as shown. The statistical and algorithms used are described elsewhere herein. Typically, but not exclusively, the output of comparators 72 and 73 are a single scalar 74 and 75 respectively for each vocalized word or phrase.

Comparator 76 compares the values 74 and 75 to perform a classification metric. One may generally view one such metric as "more positive or more negative." In one embodiment, an output value 77 may consist of "positive," "negative," or "neither." "Indeterminate" may be substituted for "neither." Note that there may be a distinction between not having enough data to make a comparison by 76, in which case there may be "no output" from 75 for a vocalization. This is distinct from "neither," which may represent that neither scalars 74 or 75 are sufficiently dominant. Output 77 may comprise more than a binary, tertiary, or scalar output. For example, other statistical metrics may also be provided such as a sigma for a Gaussian (or other) distribution; a specific statistical distribution itself; a quantity N representing a quantity of input data, or other outputs. Data 74 and 75 may comprise scalars, statistical parameters (such as mean, sigma, and the like), a statistical distribution or other metrics. The positive and negative phenotypes 70 and 71 may be further differentiated into sub-phenotypes, with downstream processing steps similarly differentiated.

FIG. 2 does not show parsing the vocalizations 67 into words or phrases. Also, FIG. 2 does not show classification of such words or phrases. This parsing and classification are included in some embodiments, and not included in others. That is, inputs 68 and 69 to comparators 72 and 73 may include anything from raw audio data to fully classified vocalization words and phrases.

An advantage and use of embodiments of FIG. 2 is that vocalizations may be broadly and reliably classed as "positive" or "negative," permitting assessment of the state of an animal or a situation in a cage. The use of vocalizations has an advantage over the detectable behaviors in that they may occur first and are likely to be more readily accessible. For example, animals may be in a nest or burrow, blocking the use of video for detection of behaviors.

Figure 3:
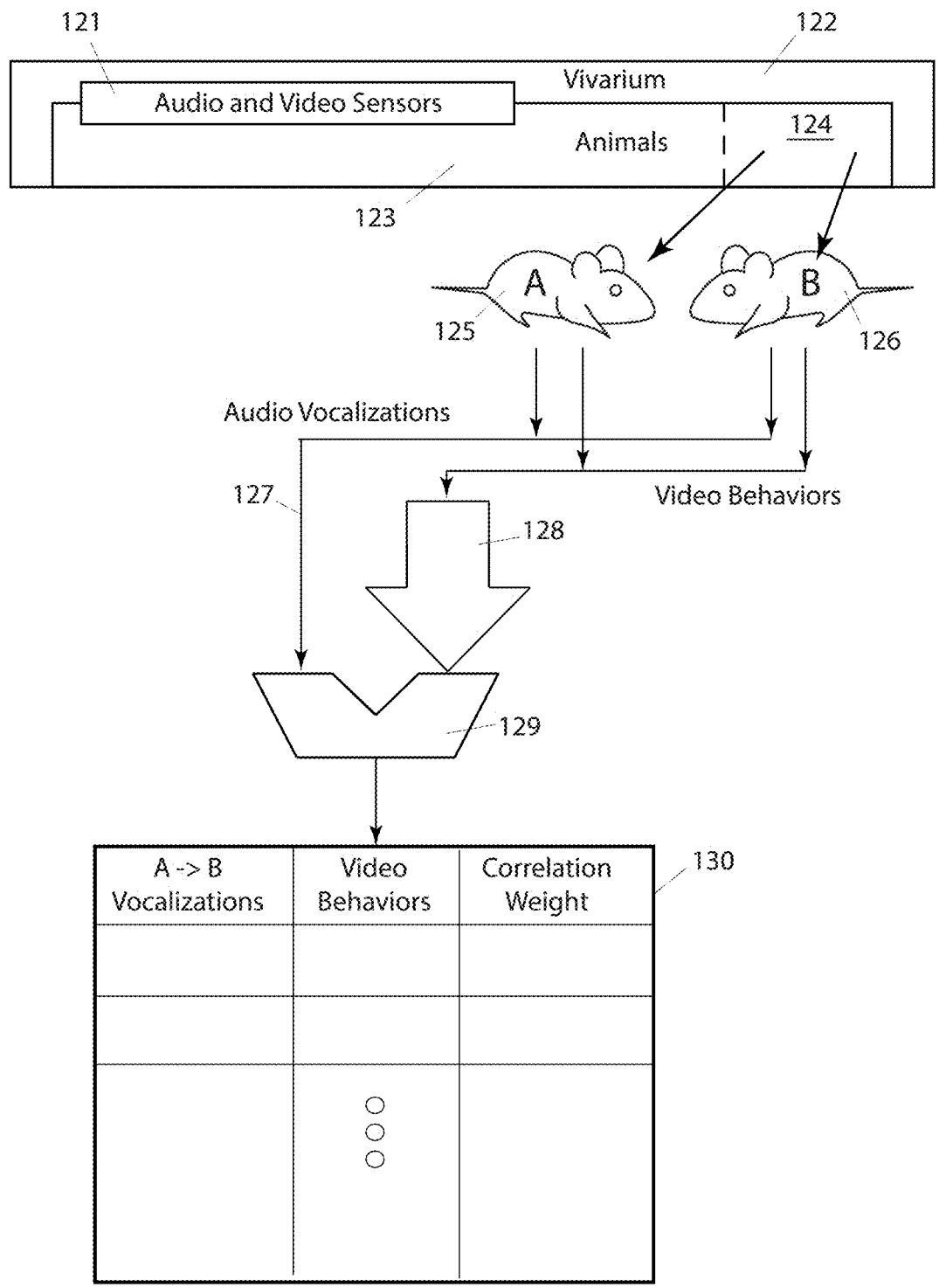
FIG. 3 A block diagram showing an embodiment of creating a table correlating audio calls and responses of two animals with video behaviors.

Turning now to FIG. 3, we see embodiments applicable to two or more rodents, typically in a single cage.

A vivarium 122 comprises animals 123 in cages. Two such rodents 125 and 126 are in home cage 124. Home cages have audio and video sensors 121 proximal to each cage. Embodiments include sensors not proximal to cages and animals not in home cages. Mice 125 and 126 generate vocalizations 127, both human-audible and ultrasonic, as detected by audio sensors 121, and stored and communicated by hardware not shown in this Figure. (Conventional non-transitory memory devices, computers and microprocessors, and network and communication equipment may be used for these purposes.) Statistical and algorithmic comparator 129 provides comparisons between the vocalizations 127 and video behaviors of mice 125 and 126. Note that a difference between these embodiments and those shown in FIG. 2 are that all behaviors, 127 and 128 are from live mice (or recorded from live mice) rather than predetermined and known phenotypes. The purpose of embodiments shown in the Figure is to associate audio vocalizations between two mice with the video behavior of one or both mice.

It is useful, for two (or more) rodents to think of vocalizations as a "call" from a first animal and a "response" from a second animal, typically as part of socialization activity. In some cases, there is missing call or missing response. Arrow 128 is larger than arrow 127, in the Figure, as a generalization that video behaviors 128 are often more complex (e.g., contain more data), than an audio stream 127.

FIG. 3 does not show parsing the vocalizations 127 into words or phrases. FIG. 3 does not show identifying and classifying video behaviors 128. Also, FIG. 3 does not show classification of vocalizations as words or phrases. These parsings and classifications are included in some embodiments, and not included in others. That is, inputs 127 and 128 to comparator 129 may include anything from raw audio and video data to fully classified vocalization and video behaviors. It is typically desirable that the inputs 127 and 128 include some preprocessing in the form of parsing and classification.

The outputs of comparator 129 are used to create a table (or multiple tables, or a database) 130. The table identifies a relationship between a vocalization call and response with a video behavior, and provides a correlation weight. There may be more than one A→B vocalization for the same video behavior. There may be more than one video behavior for the same A→B vocalization. Note that the call and response roles of animals A and B may reverse, not shown in the Figure.

In some embodiments it is desirable to know which animal, A or B, (125 or 126) generated a particular vocalization. That is, to know which animal generated the call and which animal generated the response. It is non-trivial to identify the source of ultrasonic sounds in an animal cage. In one embodiment, video behaviors are specifically used to identify which animal generated the vocalization. For example, if one animal is sleeping or drinking, while the other animal is exploring the cage, it is more likely that the exploring animal generated the vocalization. As another example, animal A may be threatening animal B. Such threats and responses, either as vocalizations or video behaviors, may be known well enough to assign a call and a response to the correct animals. Embodiments are specifically claimed that identify which animal out of two or more in the same cage generates a vocalization. In some embodiments, the table 130 provides this function, with already known correlations used to make a "most likely" assessment of which animal is generating a vocalization. In some embodiments, table 130 is used in such a "feedback" purpose, not shown in the Figure.

Comparator 129 may use a variety of statistical, algorithmic, or clustering analysis, as described elsewhere herein. Embodiments may work at the level of "words" or "phrases," as described elsewhere herein.

Figure 4:
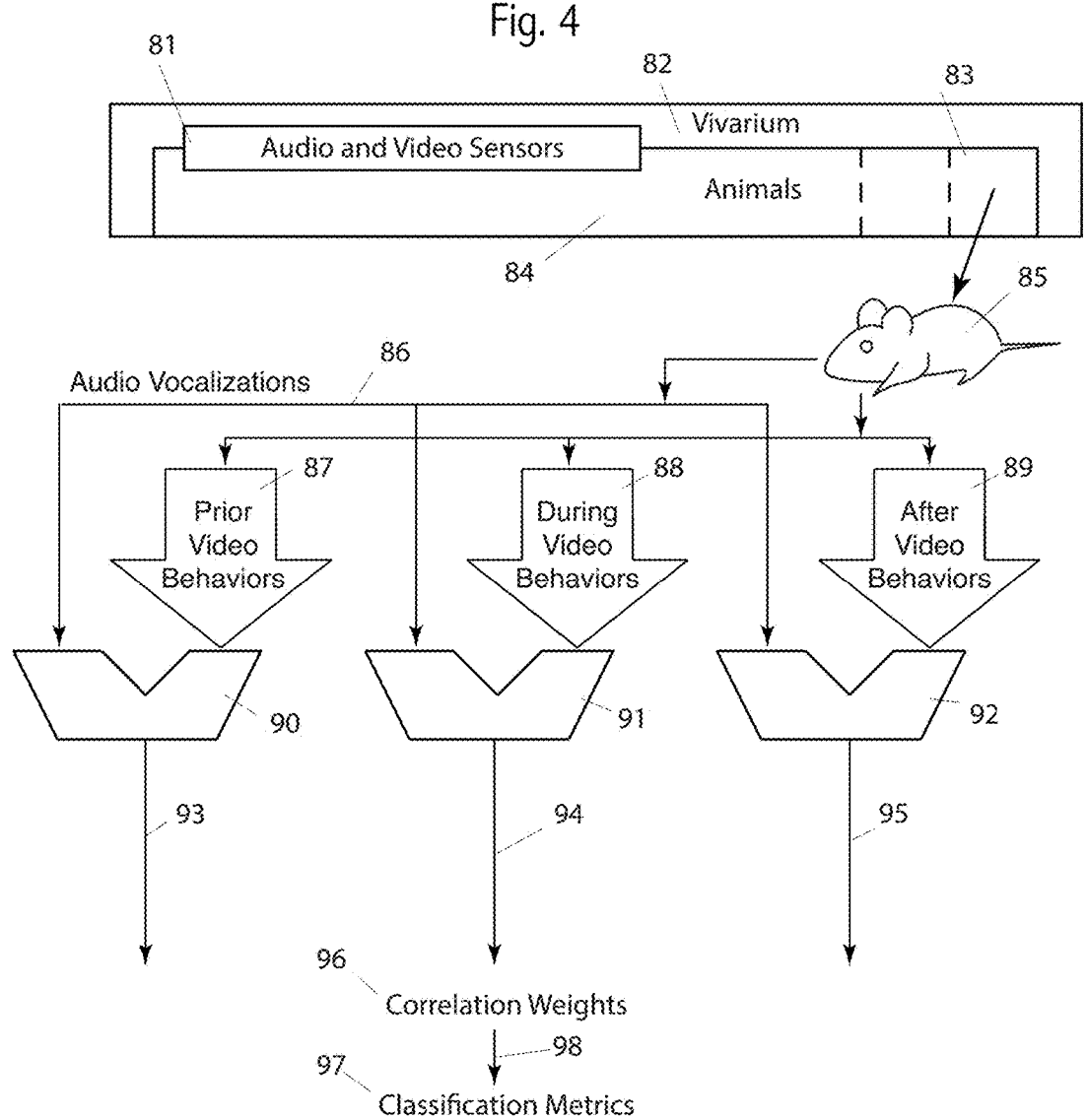
FIG. 4 A block diagram showing an embodiment associating rodent vocalizations before, during or after video behaviors.

Turning now to FIG. 4, we see embodiments that consider the time relationship between audio vocalizations and video behaviors. Such relations are particularly valuable for the predictive value and for enhancing the understanding and recognition of individual behaviors and behavior phrases.

A vocalization may occur prior to a video behavior, such as would be detected by comparator 90. A vocalization may occur simultaneously to a video behavior, such as would be detected by comparator 91. A vocalization may occur after to a video behavior, such as would be detected by comparator 92.

As in embodiments shown in FIGS. 2 and 3, comparators 90, 91 and 92 are used to compare audio vocalizations 86 with video behaviors 87, 88 and 89. Simple time-shifting, or more complex algorithms may be used to shift either the vocalization or a video behavior for the three comparisons, 90, 91 and 92. Although three separate comparators are used, a single comparator may be used and shared among these three purposes. We consider time-shifting audio with respect to video or time-shifting video with respect to audio to be the same.

A vivarium 82 comprises animals 84 in cages such as 83. Home cages have audio and video sensors 81 proximal to each cage. Mouse 85 is an exemplary animal, living in home cage 83. Embodiments include sensors not proximal to cages and animals not in home cages. Mouse 85 generates vocalizations 86, both human-audible and ultrasonic, as detected by audio sensors 81, and stored and communicated by hardware not shown in this Figure. (Conventional non-transitory memory devices, computers and microprocessors, and network and communication equipment may be used for these purposes.) Statistical and algorithmic comparators 90-92 provide comparisons respectively between the vocalizations 86 and video behaviors of mouse 85, time shifted to provide 87, 88 and 89. The audio vocalizations may be time shifted as an alternative embodiment, or both vocalizations and video behaviors may be time shifted.

Comparators 90-92 may use a variety of statistical, algorithmic, or clustering analysis, as described elsewhere herein. Embodiments may work at the level of "words" or "phrases," as described elsewhere herein.

FIG. 4 does not show parsing the vocalizations 86 into words or phrases. FIG. 4 does not show identifying and classifying video behaviors 87-89. Also, FIG. 4 does not show classification of vocalizations into words or phrases. These parsings and classifications are included in some embodiments, and not included in others. That is, inputs 86-89 to comparators 90-92 may include anything from raw audio and video data to fully classified vocalization and video behaviors. It is typically desirable that the inputs 86-89 include some preprocessing in the form of parsing and classification.

The outputs 93-95 from comparators 90-92 respectively may be scalars, statistical parameters (such as mean and sigma) or statistical distributions. All three outputs comprise some form of correlation weights 96. These correlation weights may then be used 98 to create classification metrics 97.

Although this Figure shows three distinct paths, "prior," "during" and "after," embodiments use a continuous range of times, such as by finding a peak correlation time between a time-shifted vocalization and a video behavior. That is, in some embodiments there are not three distinct paths a shown, but rather a merged path that provides a "most likely" delay (positive or negative) from a vocalization to a video behavior.

An embodiment, not shown in this Figure, uses the outputs from 96, 97, or both to create state diagrams with state transitions, not shown. Behaviors, either audio or video, may be either transitions between such states, or the states themselves.

Figure 5:
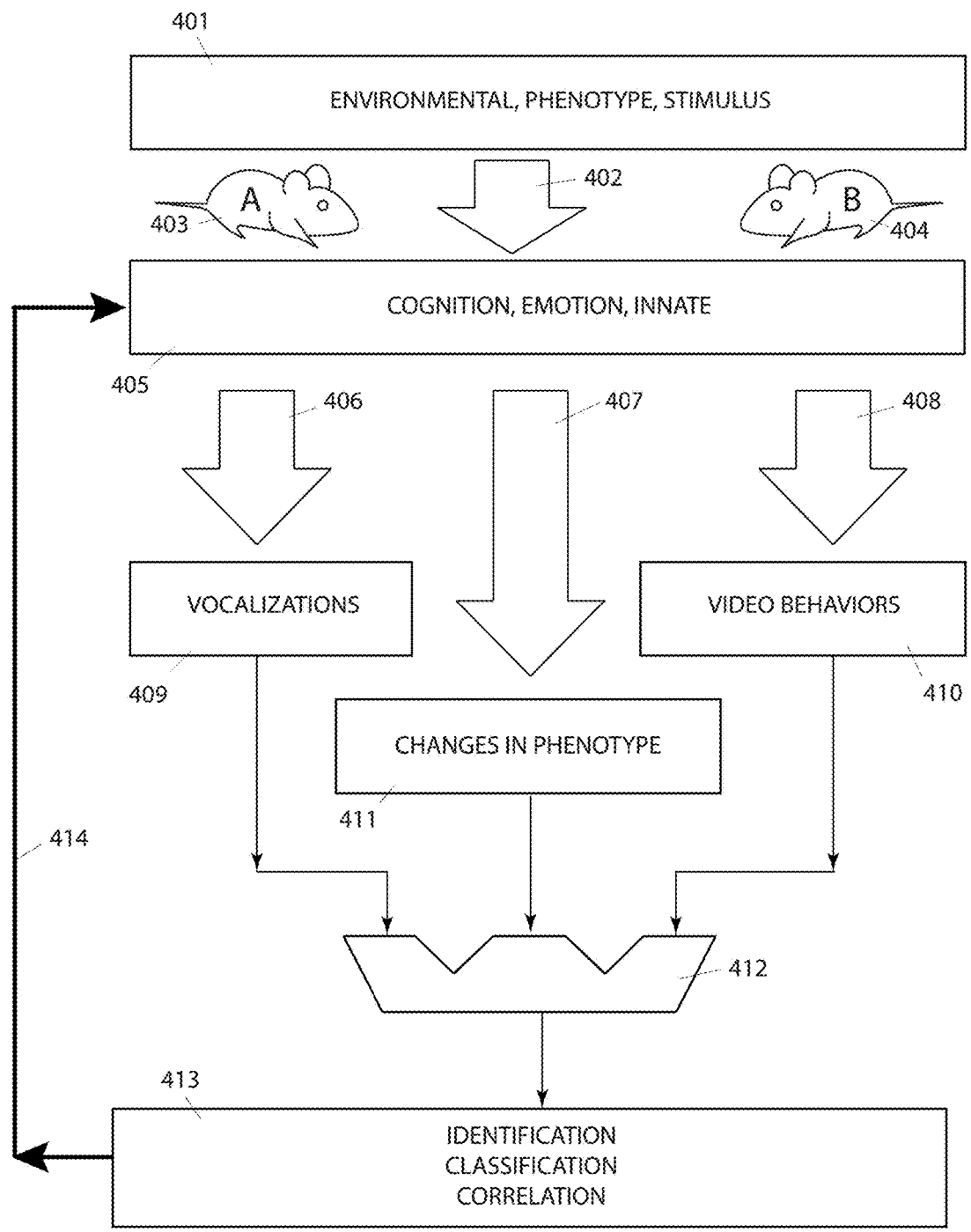
FIG. 5 A block diagram showing statistical analysis to identify, classify and correlate aggregate behaviors and changes to phenotypes with animal cognition, emotion, and innate characteristics.

Turning now to FIG. 5 we see embodiments that consider an aggregate of behaviors including behaviors identifiable by visual observation, vocalizations, and changes to an animal's phenotype. Such changes to the animal's phenotype may include broadly defined characteristic of the animal other than specific visual behaviors and specific vocalizations. Changes to blood chemistry, urine chemistry, behavioral patterns, and longer-term changes are included as part of a phenotype. One might broadly view behavior as occurring in one of two pathways. First, an animal becomes aware of something. We refer to that awareness as cognition. That cognition then drives emotion, which then produces a particular behavior or set of behaviors. The second pathway we refer to as innate. Innate responses to stimuli, or innate behaviors do not require a cognition step, and may not involve any identifiable emotion, per se. For example, a startle response might be viewed as innate.

It is desirable to know what an animal is thinking, or what it is feeling. We know that mammals and particularly rodents exhibit many of the same behaviors as humans. We also know that these behaviors in humans are associated with certain thinking or emotional states. We might assign, as it were, the same cognitive or emotional states to the animal, based on association with observable behaviors. It would then be desirable to ascertain if the animal is "thinking" or "feeling" one of these states, even if the associated behavior was not immediately detectable. This is valuable when trying to assess the positive or negative effects of a drug or therapeutic treatment in a study, particularly for therapies that are known or suspected to have psychoactive properties.

In FIG. 5, we start with known environmental states, a known animal phenotype, and any stimulus, 401. Two exemplary animals, such as two mice, 403 and 404 are shown. Embodiments may use more or fewer than two animals. Given the starting states 401 of animals 403 and 404 in a study, we may know or assume starting cognition, emotional, and innate behaviors, 405. This initial knowledge or assumption is shown as 402.

From this starting state 405, we may then observe vocalizations 406, video behaviors 408, and changes to phenotype 407. By "observe," we mean automated collection of data from sensors, including those discussed elsewhere herein and shown in FIGS. 2-4. Raw data from the sensors in analyzed and categorized as described in other embodiments herein, becoming identified vocalizations 409, identified changes in phenotype 411 and identified video behaviors 410. These aggregated and classified behaviors 409, 401 and 411 are then analyzed 412. We refer to the combination of 409, 410 and 411 as "aggregated behaviors." Methods of analysis are discussed elsewhere herein, and include correlation, clustering, best-fit, distance-determining algorithms, and other statistical methods. The output of step 412 is the identification, classification, or correlation, or any combination of the aggregated behaviors, in particular, to assign them by weight, correlation or prediction to one or more cognitive or emotional states, or innate behavior.

For known cognitive or emotional states, or innate behavior, we then have detailed association 413 with aggregated behavior. In some embodiments, the identification, classification and correlation 413 may then be used to determine cognitive or emotional states, or innate behavior, including those that were not known in advance, or modifications to those known in advance. This is shown by arrow 414. Key embodiments include this "feedback" 414. That is, automated observations 406, 407 and 408 ultimately produced more knowledge 413 that may be used to determine, or at least assign names to, cognition, emotion, and innate states or activity. These embodiments then allow us to "know what an animal is thinking or feeling." This information allows to update 405 and then, for future studies, start with higher quality knowledge or assumptions 401.

One set of eight "behavioral affective states" is: arousal, excited, happy, calm, quick, sleepy, unhappy, and fearful. In some embodiments, this set, or another set similar (subset, superset) may be the key states in 405. A goal of embodiments is to consistently identify one or more such states, based on the vocalizations, changes to phenotype and video behaviors, 409, 411 and 410. Embodiments are specifically claimed that use any or all subsets of the eight behavioral affective states, such as in Markov sets.

The steps in FIG. 5 may be performed in real-time, or they may be performed using previously recorded data, or a mix of the two.

Figure 6:
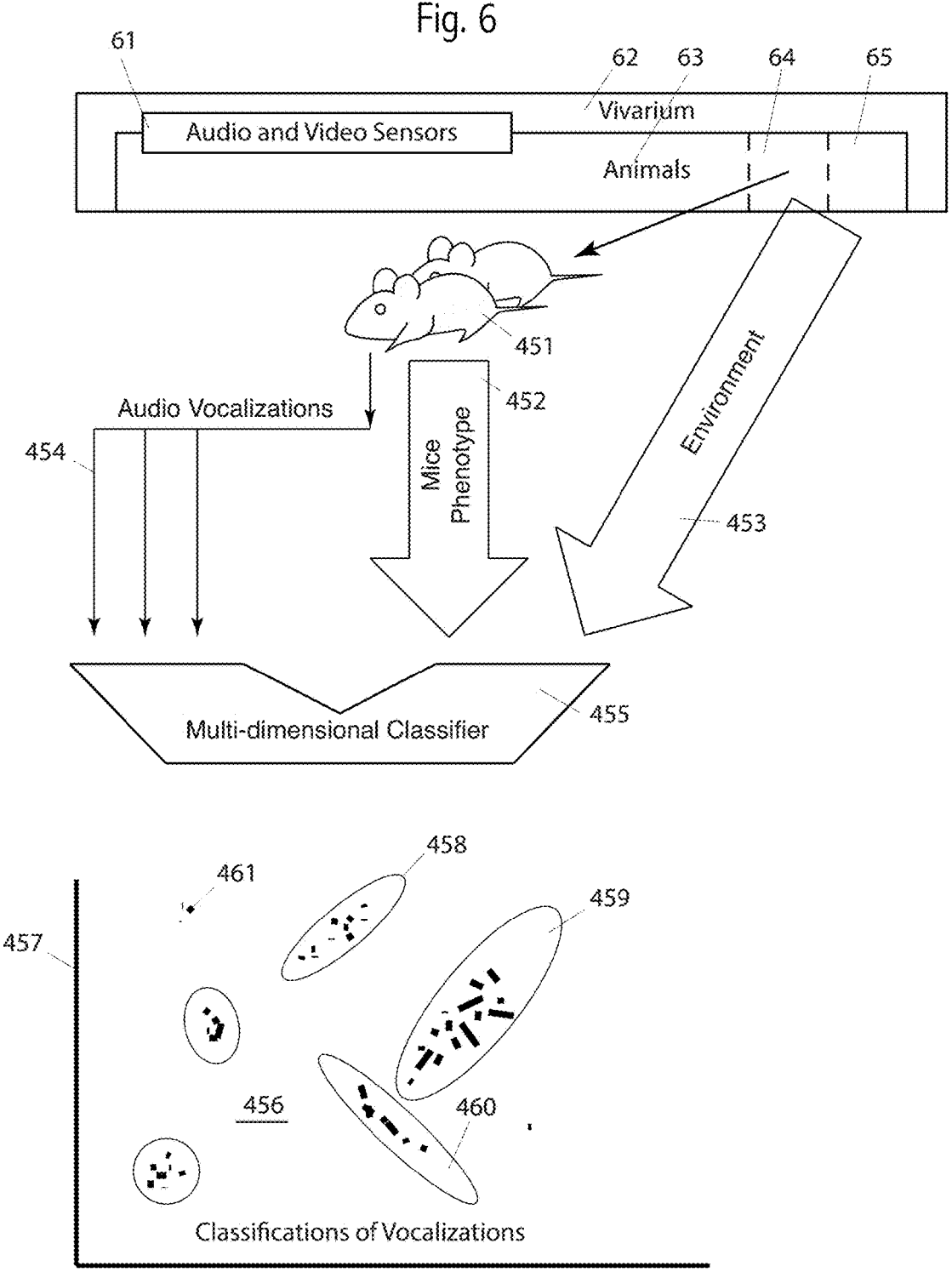
FIG. 6 A block diagram showing classification using statistics, multi-dimensional analysis, and clustering of audio vocalizations, phenotypes, and environment to identify and classify clusters of vocalizations.

Turning now to FIG. 6, we see embodiments that use multi-dimensional clustering as a method of classifying vocalizations. Some embodiments, not shown, also use video behaviors or audio behaviors as one or more dimensions for the clustering classification.

A vivarium 62 comprises animals 63 in cages 64 and 65. Home cages have audio and video sensors 61 proximal to each cage. Mouse 451 is an exemplary animal, living in home cage 64. There may be more than one rodent in a home cage. Embodiments include sensors not proximal to cages and animals not in home cages. Mouse 451 generates audio vocalizations 454, both human-audible and ultrasonic, as detected by audio sensors 61, and stored and communicated by hardware not shown in this Figure. (Conventional non-transitory memory devices, computers and microprocessors, and network and communication equipment may be used for these purposes.)

A known mouse phenotype is shown 452. The environment affecting the mouse 451 or cage 64, such as cage husbandry attributes and other environmental factors, is shown 453. The aggregate of the vocalizations 454, the mice phenotype 452 and the environment 453, are identified as the aggregate input to the multi-dimensional classifier, 455. Large open arrows are used for the mouse or mice phenotype 452 and the environment 453 to show that these are typically large datasets comprising numerous parameters, which are frequently but not exclusively known beforehand or predetermined. The audio vocalizations 454 are shown as multiple narrow arrows to indicate multiple vocalizations from animal 451, typically but not exclusively in the form of audio data. In some embodiments the vocalizations have been preprocessed, not shown, into identified audio "words" or "phrases."

The purpose of the multi-dimensional classifier is to use clustering or other statistical methods to identify clusters of repeated input from the aggregated input. Each such cluster might be considered an "identified behavior," which include vocalization as a key attribute. These identified behaviors may or may not correspond with well-known behaviors, such as grooming, exercising, and the like. Known, named behaviors are discussed elsewhere herein. We use the term "identified" because the multi-dimensional classifier 455 identified a cluster.

It is difficult, as is known it the art, to provide a two-dimensional image of how a multi-dimensional classifier, such as one using any of many known clustering algorithms, works or provides output. Here, in graph 456 a minimal representation of an output the classifier 455 is shown. The axes 457 are arbitrary and represent any of many possible dimensions, or attributes of input to the classifier. For example, one dimension might be cage temperature. Another dimension might be the heart rate of the animal, or the animal's weight. Yet another dimension might be the pitch of a vocalization. Indeed there may be dozens or even hundreds of such attributes as inputs to the classifier and thus dimensions in the automated analysis. Here five clusters are shown, each as a set of points in an ellipse. Three are identified as 458, 459 and 460. The ellipses schematically represent the bounds of a cluster, as determined by the classifier 455. Such bounds are typically statistical distributions in multiple dimensions, not a solid dividing line between "in" and "out" of the cluster, as shown in the Figure. Cluster 459 is a large cluster with many data points. Cluster 458 is a smaller cluster with fewer data points.

Cluster 460 has a "shape" similar to a line. Such a line has similarity to a line in a two-dimensional graph, often used to show a best-fit relationship between a single input variable (scalar) and a single output scalar. Such "best fit" lines are common in medical research reports, typically reported with a correlation coefficient, or "r." The clustering algorithm may also output an "r" for each cluster, although often the multi-dimensional aspect makes the "quality" of the cluster harder to measure uniformly than a basic "r." Two additional clearly visible clusters are shown in ellipses, but not identified with reference numbers. Typically data contains "outliers"—data points that do not fit well into any cluster. Exemplary outliers are shown, 461.

It is useful for a clustering algorithm to identify the bounds of a cluster such that they don't overlap, or don't extensively overlap. For example, a portion of cluster 459 is quite close to a portion of cluster 460. An advantage of such isolation is that each cluster may be given a name, such as "anxious," or "sleepy." Then for a given behavior, such as a vocalization, in a known environment with a known or determined phenotype, it is convenient to say that this behavior identifies the animal as "anxious," or "sleepy." Again, such bounds and cluster identification is actually in the form of statistical distributions. However, a simple name is a valuable convenience. Clustering algorithms, and most other statistical methods as part of the multi-dimensional classifier 455, are most effective with large input datasets. For example, it may be desirable to use hundreds of hours of recorded vocalizations from each of hundreds of mice, across a range of different phenotypes.

Clustering algorithms in the art are discussed in Wikipedia, such as: https://en.wikipedia.org/wiki/Cluster_analysis, and also discussed elsewhere herein.

Some embodiments of compare methods, steps or devices use algorithms for computing "distance." These include, as non-limiting examples, L1, L2 and Metropolis distances.

Compare methods or steps often use feature identification, feature mapping, and feature extraction algorithms such as: HAAR, ORB, SIFT, SURF, Neural nets, convolution, FAST/BRIEF, STATA, convolutional neural nets, Pierson correlation, Tanimoto coefficients, a Jaccard index, Tsallis mutual, entropy measurement methods, clustering algorithms, Hough transforms, and clustering algorithms or cluster analysis. Additional feature extraction algorithms are identified and discussed here: https://en.wikipedia.org/wiki/Feature_extraction. Feature extraction methods may be used to locate vocalizations within raw or minimally filtered audio data. Feature extraction algorithms may be generally grouped as one or more of: edge detection, corner detection, blob detection, ridge detection, and scale-invariant transforms.

A K-means clustering or nearest neighbor algorithm is often a good choice or staring point for applications and embodiments discussed or claimed herein.

General criteria when analyzing vocalizations include:
animal species;
animal type, e.g., strain or genetic profile;
gender;
age, e.g., maturity;
cage mates;
environment, including husbandry attributes.

Specific criteria for clustering, classification, and identification of vocalizations words and phrase include:
average pitch (in KHz, for example);
slope of pitch (in KHz per second, for example);
band of the pitch (for example, a known lower band or upper band);
shape (see non-limiting example in Figures);
time length of word or phrase;
gap (silence) between phrases;
gaps (silence) within phrases;
multiple simultaneous pitches;
amplitude or intensity (loudness);
number of words in a phrase;
relationship to other phrases, such as a superset;
abundance—within a total sample cohort;
abundance—within a predetermined time window;
neighboring word or phrase, immediately before or after;
number of sequential repeats;
in one or both of predetermined frequency bands;
association with a known video behavior;
association with a known socialization behavior, such as grooming and the like;
association with a known, externally provided stimulus;
time of day;
association with direction of the animal's gaze;
association with a call or response of a cage mate;
association with a body pose as detected by video data;
association with a sequence of body poses as detected by video data;
association with drinking;
association with eating;
association with exercising;
response after the vocalization by a cage mate (either audio or video);
in response to a an immediately previous call by a cage mate;
association with a learned or adaptive behavior.

Any and all combinations of the above criteria are specifically claimed as embodiments, with or without the inclusion of other behaviors. Any and all combinations of the above criteria are specifically claimed as Markov sets, with or without the inclusion of other behaviors.

One upper frequency range of mouse vocalizations is 55-90 KHz. One lower frequency range of mouse vocalizations is 50-75 KHz. Other frequency bands may be determined by audio analysis using the same vivarium environment and same study type as animals in a study.

An advantage of clustering algorithms is that they may be fed as input sufficient data to identify one or more above possible criteria. Then, a clustering algorithm will identify which criteria produce clusters. It is then these criteria that are useful of identification or classification, or for use as intermediate data to another method step. In general, as useful criteria are so identified, clustering may be run again ignoring the less useful criteria. This reduces the number of dimensions to consider in the algorithm and likely reduces noise or outliers. One method or goal is to continue to eliminate less useful criteria until only a small number of useful criteria remain. Then, each remaining cluster may be assigned an identifier, such as a name or number. Then, new vocalizations may be rapidly identified as one vocalization in this known set, using a simpler algorithm, such as a correlator. Such cycling of one or more clustering algorithms for identification of useful criteria, and then using the final clusters to create a "known set" of vocalizations are specifically claimed as embodiments.

Embodiments are specifically claimed that encompass any or all embodiments shown in FIGS. 2-6, and 9. In fact, in a non-limiting example, embodiments in FIG. 2 may be used of an initial course classification of vocalizations. Often, the most important vocalizations are those that correlate strongly to either positive or negative phenotypes. Then, embodiments in FIG. 4 are used to associate vocalization behaviors with video behaviors, of isolated animals. This permits classifying vocalizations with known video behaviors and phenotypes associated with video behaviors (of which there are many known). Then, embodiments in FIG. 3 may apply this knowledge to further understand the relationship between two or more animals. Then, using knowledge of calls and response, vocalizations of isolated animals may be better understood. For example, a "friendly" call that generates a "friendly" response, when used by an isolated animal may be an indication that the animal is lonely and would like company.

Figure 8:
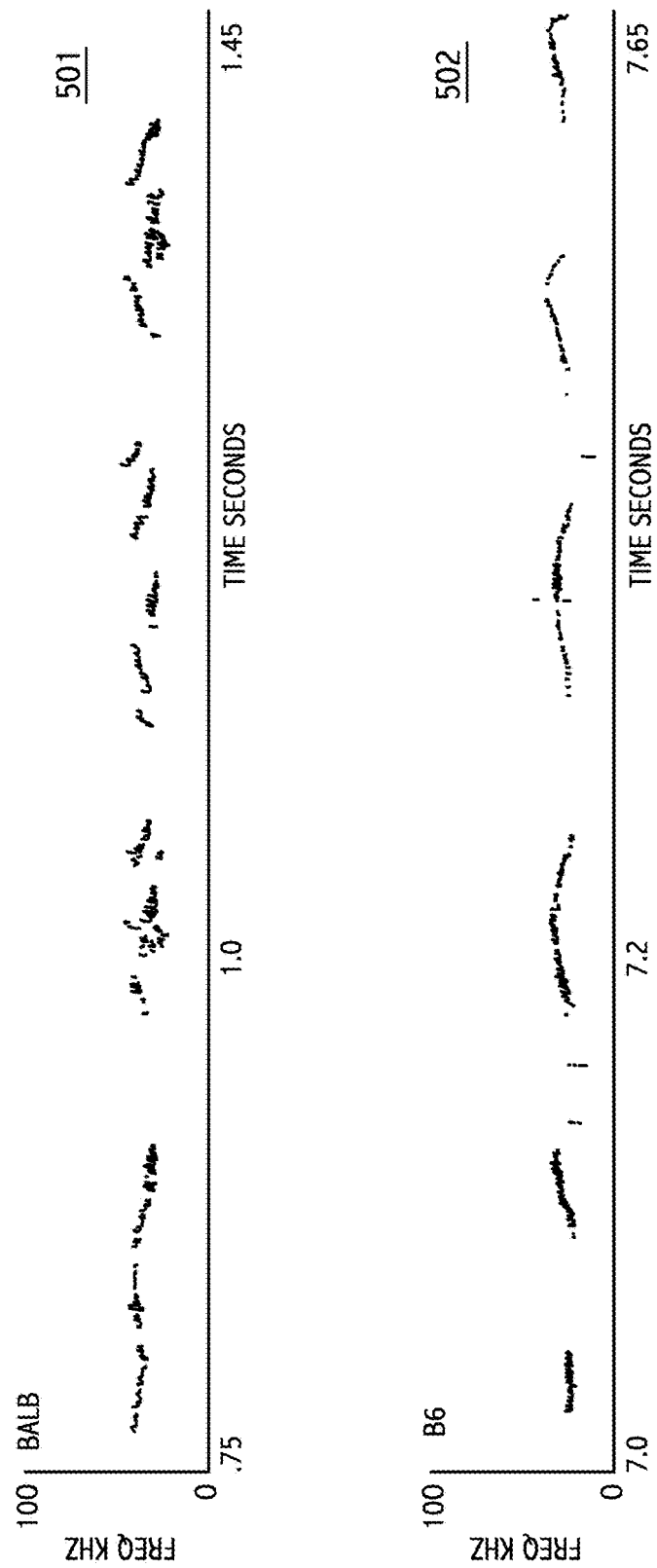
FIG. 8 Prior art in the field of mouse prosody showing differences in vocalizations between two types of mice.
Figure 9:
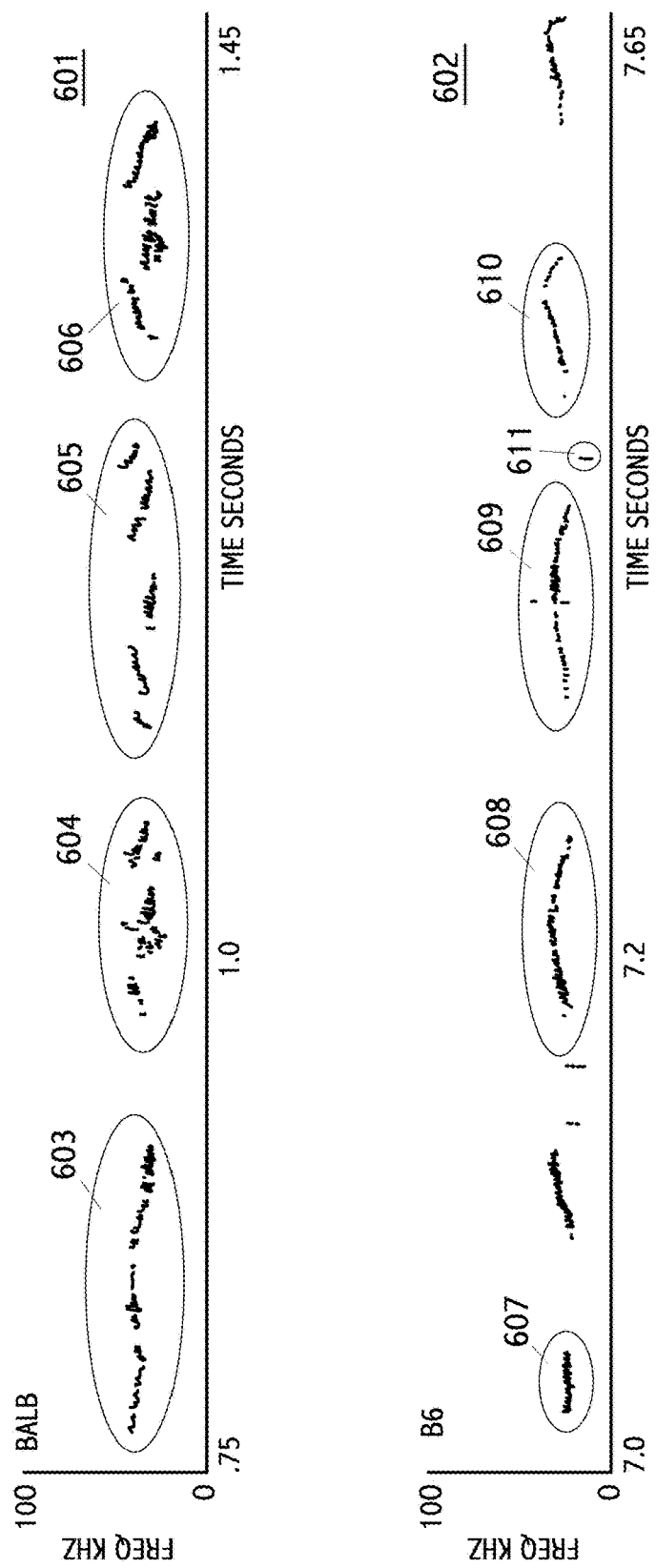
FIG. 9 Frequency v. time graphs showing categorization of mouse vocalizations.

FIG. 9 spectrograph 602 shows vocalization from mouse type B6, from FIG. 8 as 502, with identification of phrases 607-610 not in the prior art. These phrases are distinct from phrases of the BALB mouse. They generally have no pause or a shorter pause. Average pitch is lower. Pitch change is minimal. Multiple simultaneous pitches are not present. Overall shape of phrase is flat, or with a slight upward and then downward slope. Repeated phrases are visible. For example, 608 and 609 are clearly similar in length, pitch, and shape. Spectrograph recordings contain noise, such as shown as 611. Automatic classification and identification methods need to identify both similar phrases, such as 604 and 606; and 608 and 609, as well as eliminate noise, such as 611. Clustering algorithms, as discussed elsewhere herein, may be used to identify vocalization words or phrases, such as shown in FIG. 9.

Prior Art

Figure 7:
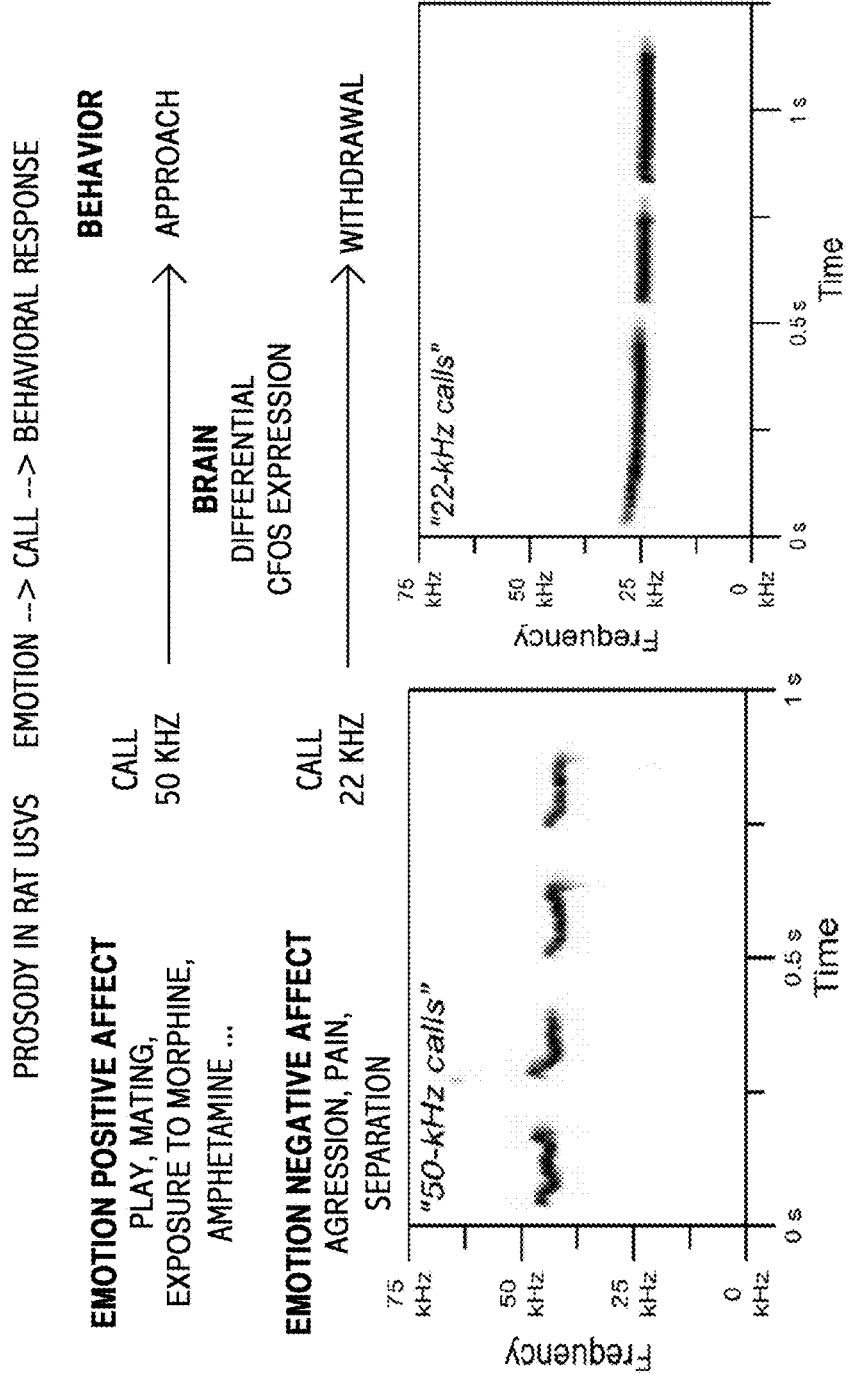
FIG. 7 Prior art in the field of recording ultrasonic rat vocalization calls around 22 KHz and 50 KHz and associating these with positive or negative emotions.
Figure 10:
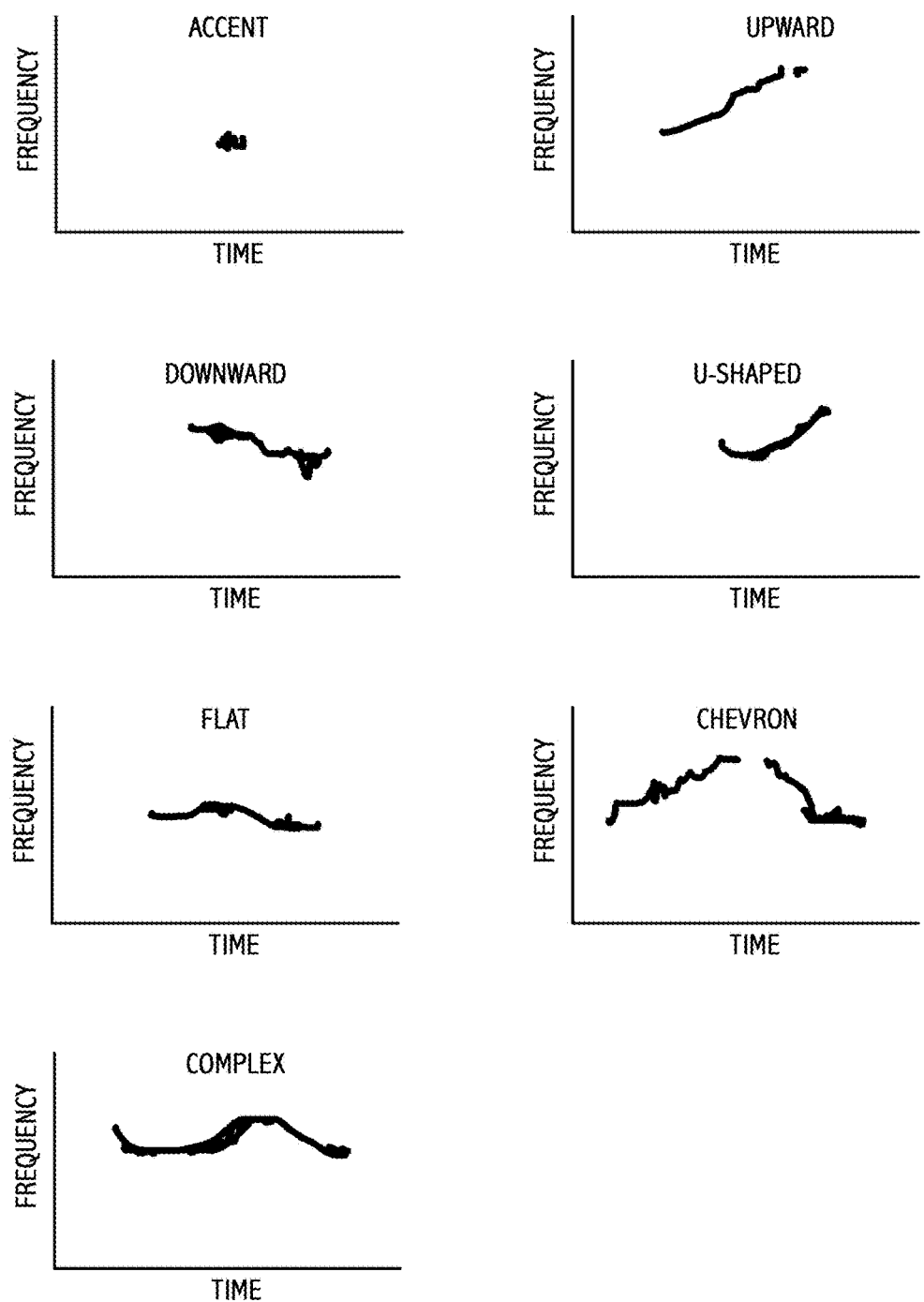
FIG. 10 Prior art showing classification of vocalizations into seven shapes.

Prior art is shown in FIGS. 7, 8, and 10. These figures are adapted from a 55-page slide set by Garet Lahvis, Department of Behaviors Neuroscience, Oregon Health and Sciences University, Portland Oreg. Figure data and detail in the original work is necessary missing due to the crude, out-of-date and historically inconsistent limitations of US patent drawings.

FIG. 7 shows vocalization prosody in rats. Two recordings are shown. The first is related to "emotional positive affect," at roughly 50 KHz. [The use of "affect" rather than "effect" is a term of the art. However, in English, this usage is sic.] The second is related to "emotional negative affect," at roughly 22 KHz. The figure or data is credited to Sadananda et al., Neuroscience Letters, 2008; and Burgdorf et al., Journal of Comparative Psychology, 2008.

FIG. 8 shows additional vocalization prosody in mice. Two recordings are shown. Recording 501 is for mouse type BALB. Recording 502 is for mouse type B6. A number of differences between the vocalizations of the mouse types are visible. The BALB vocalizations are generally higher in pitch than the B6 vocalizations. The BALB vocalization "phrases" shown in added ellipses, are more broken, with distinct "words," compared to the B6 vocalizations. The BALB vocalizations also show more simultaneous pitches than the B6 vocalizations. The vocalization spectrograph data ("scribbles" in the Figure) are in the original work, as are the time scales and frequency (pitch) scales. Quantization of pitch, amplitude and duration, as they vary by rat strains, is discussed in the prior art.

FIG. 10 shows prior art classification of vocalizations into seven named categories. The prior art does not teach how to select such classifications. The naming suggests that the classification were done manually. These are shown without scale.

Additional Embodiments

FIG. 9 shows an embodiment were prior art records of mouse vocalizations (see FIG. 8) have been used to identify vocalization words or phrases. 601 is a prior art spectrogram with four identifications added, shown as 603-606. 602 is a prior art spectrogram with four identifications added, shown as 607-610. Note that the BALB vocalization phrases typically contain more distinct words than B6 vocalizations, such as visible in 604-606. In this Figure, phrases are recognizable. Note that 604 and 606 are similar, both with three words, the first rising in pitch, the second comprising multiple frequencies, and the third dropping in pitch, with pauses between the words. The length of the two phrases is also comparable. Phrase 605 maybe considered as the phrase of 604 and 606 with a short prefix and suffix word added. Phrase 603 is clearly different, with almost no pauses and an overall downward pitch slope, with minimal simultaneous pitches. Note that these phrases and words are not well characterized by the seven named shapes in the prior art shown in FIG. 10.

Vivariums house a number of animals, typically test or study animals, such as mice, in a number of cages, often thousands of cages. The study animals are frequently used to test drugs, genetics, animal strains, husbandry experiments, methods of treatment, procedures, diagnostics, and the like. We refer to all such uses of a vivarium as a study.

Of particular interest to embodiments of this invention are studies, using a vivarium, to test drug efficacy, to test and quantify side effects, to observe, quantify and classify animal behaviors, and provide studies for use in personalized medicine. Of particular interest are drugs and other treatments for cancer, or more generally, neoplasms. Of particular interest are brain cancers.

As stated above in the Summary section, many tumors are characterized with morphology where neoplastic cells form a tumor mass and that mass grows in the subject (animal or human). When the mass reaches a certain size it often interferes mechanically with the function of the organ or of the location in the organ, particularly so for the brain, where the tumor mass is located. Such interference eventually results in a behavioral difference of the subject.

We define, for this specification, the term "behavior" broadly. First, the singular form of the word, behavior, and the plural form of the word, behaviors, mean effectively the same thing and may be used interchangeably, unless clearly indicated by the context otherwise. Second, behaviors may be internal or external. For example, we consider changes in blood chemistry, changes in urine, changes in exhaled air, and the like, to be behaviors. They are measurable attributes of the animals in the study and are subject to alteration depending both on the state of the tumor and nature of the treatment. Internal behaviors may also be called or classified as physiological parameters, or biological metrics, such as blood chemistry or urine chemistry.

For convenience, we define "audio behaviors" as any behaviors that may be automatically detected and identified, at least in part from audio data from an animal cage. For convenience, we define "video behaviors" as any behaviors that may be automatically detected and identified, at least in part from video data from an animal cage.

Video behaviors include but are not limited to:
performing a stereotypical "nose poke;"
touching its nose to a specific spot on the cage wall, e.g. one behind which there is a green LED not a blue one, or behind which there is the led that is different from the other two;
running on the running wheel for predetermined amount of time or device revolutions;
interacting with another animal in a specific way;
mating, grooming, fighting or parenting;

performing a physiological action or behavior related to increasing or decreasing body temperature; or the lack thereof;
selecting one food or drink source over another;
resisting eating or drinking;
eating or drinking;
human-audible or ultrasonic vocalizations, or no vocalization.

Behaviors also include patterns, frequency, and temporal and special associations with other behaviors.

Internal behaviors include but are not limited to:
urine components, including pH and protein markers;
breathing rate and patterns, such as normal, wheezing, coughing, panting, and the like;
heart rate and patterns; such as arrhythmia;
body temperature;
blood conditions observable as jaundice, or color changes in the eyes or gums; and
conditions observable as skin or fur changes.

Some internal behaviors may be detected by the use of video, and thus are then also considered video behaviors.

Embodiments are specifically claimed that incorporate any or all subsets of the above lists, such as in Markov sets.

Innate behaviors or innate characteristics are a broad terms that may include genetic or evolutionary adapted parameters or behaviors. Desire for water, food, and mating may be considered innate, along with curiosity, burrowing, chewing, nocturnal preference, body temperature and the like. The environment, conditioning, drugs, genetic alterations, disease, or other causes may modify innate behaviors. There is no bright-line distinction between innate behaviors and behaviors of a healthy animal; nonetheless, such terminology is useful and used in the art.

Behaviors associate with disease or improperly operating organs are numerous and widely known in the art. On such example is a tremor. Another such example is death. Yet more examples include changes to the healthy behaviors listed above. Embodiments of this invention identify new behaviors associated with disease or improperly operating organs.

Some embodiments do not use a vivarium. For example, animal studies or subjects using livestock, research animals such as monkeys or rabbits, wild animals, or pets may be performed in other environments such as on a farm or ranch, in an animal production environment, a home, a hospital, a veterinary clinic, or the wild.

It is desirable to keep vivarium animals in sterile cages. It is also desirable for sterility and for practical reasons such as cost, maintainability, and keeping foreign material out of the cage, to use a cage with no electrical penetrations.

Therefore, it is also desirable to implement sensors and heating methods that are free of electrical penetrations of the cage.

Rodents are prone to chew on almost every material in their cage. Thus, keeping sensors and electronics outside the cage is particularly important. Sensors and electronics external to cages is an important and novel aspect of some embodiments.

When tracking the behavior of animals in a study it is important that each animal can be identified uniquely and reliably. This is not a trivial problem, particularly in an automated environment and particularly in one using monoclonal animals that may appear virtually identical. Therefore, we discuss automated identification methods and such methods are important and novel in some embodiments.

Various methods of identifying an animal are used in different embodiments. One method comprises short-distance RFID, which may use animal ear RFID tags or embedded RFID tags and RFID sensors outside the cage. Another method comprises using video for identification, which may use animal size, coloration, unique natural or artificial body elements, such as body modifications or affixed tags, for example, to provide or to assist in the identification. Another method comprises use of an animal scale: animals of distinct weights may be identified when that animal is on the scale. Yet another method uses bar codes or other artificial markings, which may be tattooed on the animal's tail or other location. Such bar codes may be read via cameras and bar code recognition software. Yet another method uses ear notches, which may be read via cameras and image recognition software.

Another method of identifying an animal is to combine technologies. For example, an animal may be first identified using an RFID when the animal is within a small RFID range, and then tracking the movement of that animal using video tracking software. Yet another method is by exclusion: if all of the other animals in a cage are identified, then the one remaining animal is also identified.

Yet another method to identify animals is by the sounds they make.

Yet another method to identify animals is by observing behavior unique to that animal.

Various methods are used in various embodiments to detect the location of an animal in a cage. One method uses short-range RFID. For example, RFID sensors may be placed at one or more locations around the perimeter of a cage, such as at the corners, of the center of the sides, and the like. When an animal comes within range of a sensor its location is then known.

Another method of detecting the location of an animal is by activity on a device, such as an exercise wheel, or on a scale. Such a device may be fully wireless, such that animal weight data or exercise data may be collected automatically, continuously or continually, without any human, manual input. In some embodiment the exercise wheel is disposable. In some embodiment the scale is sealed such that its exterior may be sterilized between studies, and the scale re-used. In some embodiments the scale is free of components physically accessible to the animals in the cages that can be chewed by the animals in the cages.

Yet another method of detecting the location of an animal is the use of an animal sensor outside of the cage, with a directional range or a short range. Examples of such detectors include thermal detectors, capacitive sensors, and motion sensors.

In some embodiments, the identification and location of an animal may be combined using the same sensor or technology, or by using overlapping elements of sensors. For example, a single RFID sensor may be used to both identify an animal and know that it is within range of the sensor. As another example, a single video signal from a single camera may go to two separate image processing elements, one for animal identification and one for animal location.

In some embodiments, real-time animal tracking within the cage may be used as part of both identification and location. For example, if an animal has a known ID and a known location, by tracking the location of the animal within the cage the ID remains known and the tracking algorithm updates the location.

Unique improvement over the prior art in some embodiments is the use of home cages (or primary cages) for all or most of the study interactions with the animals, as contrasted with moving the animals from home cages to experimental cages or observation cages, as in the prior art.

In yet another embodiment, animals are housed singly. All references, claims, drawings and discussion applicable to multiple animals in a cage also apply to a single animal in a cage, where multiple animals are not essential to the reference.

Examples of animal behavior include but are not limited to:
- performing a stereotypical "nose poke;"
- touching its nose to a specific spot on the cage wall, e.g. a spot in front of an external green LED, rather than a blue one, or a spot in front of an LED that is a different color than two other LEDs;
- running on the running wheel for predetermined amount of time or device revolutions;
- interacting with another animal in a specific way;
- mating, grooming, fighting or parenting;
- performing a physiological action or behavior related to increasing or decreasing body temperature; or the lack thereof;
- sounds: type, frequency or volume; or the lack thereof;
- selecting one food or drink source over another;
- resisting eating or drinking;
- eating or drinking;
- normal or abnormal gait;
- normal or abnormal urine components;
- behavioral patterns or frequency;
- weight gain or loss.

Additional animal behaviors are described elsewhere herein.

Embodiments are specifically claimed incorporating any and all elements of the above lists, such as in Markov sets.

A first crux of an embodiment is to measure the behaviors of the animal, where that behavior is associated with the location of the tumor mass.

In order to quantitatively measure the behavior of a set of animals in a study, it is necessary to have baseline behaviors. A baseline behavior set may be negative (healthy animals) or positive (animals with a known tumor). Such baseline behaviors may be known in the art, or may be measured as part of embodiments, or as part of a study.

In addition, it is necessary to quantitatively observe behaviors. Although such behaviors may be observed manually, manual observation and analysis is not practical within a study of the magnitude necessary to quantify a treatment and receive approval for such a treatment on humans. Manual behavior observation suffers from the following weaknesses: (1) it is not consistent from observer to observer and not consistent for even the same observer; (2) it is difficult for an observer to quantify an observed behavior; (3) the frequency of observation is low, such as daily; (4) observation cannot be realistically continuous; (5) observation cannot be done practically in many ideal environments for the animal, such as in darkness; (7) humans cannot hear ultrasonic vocalizations As a result of these and other weaknesses of manual behavior observation, such observation has not been described in the prior art for the purpose of quantitative assessment of tumor size based on behavior at the scope and consistency required for treatment testing and approval.

Therefore, it is necessary to automate behavior observation. Such automation uses, in some embodiments, one or more electronic cameras mounted proximal to every animal cage. The camera images are communicated to a computer system where software first analyzes the images to extract desired behaviors, then analyzes the extracted behaviors to create quantitative measurements with respect to the baseline behaviors, and then the results are communicated or displayed. Some embodiments use electronic, communicating sensors other than cameras, such as motion detectors, animal location detectors, carbon dioxide detectors, ammonia detectors, husbandry parameter measurement devices, exercise monitoring, temperature monitoring, and the like.

Figure 11:
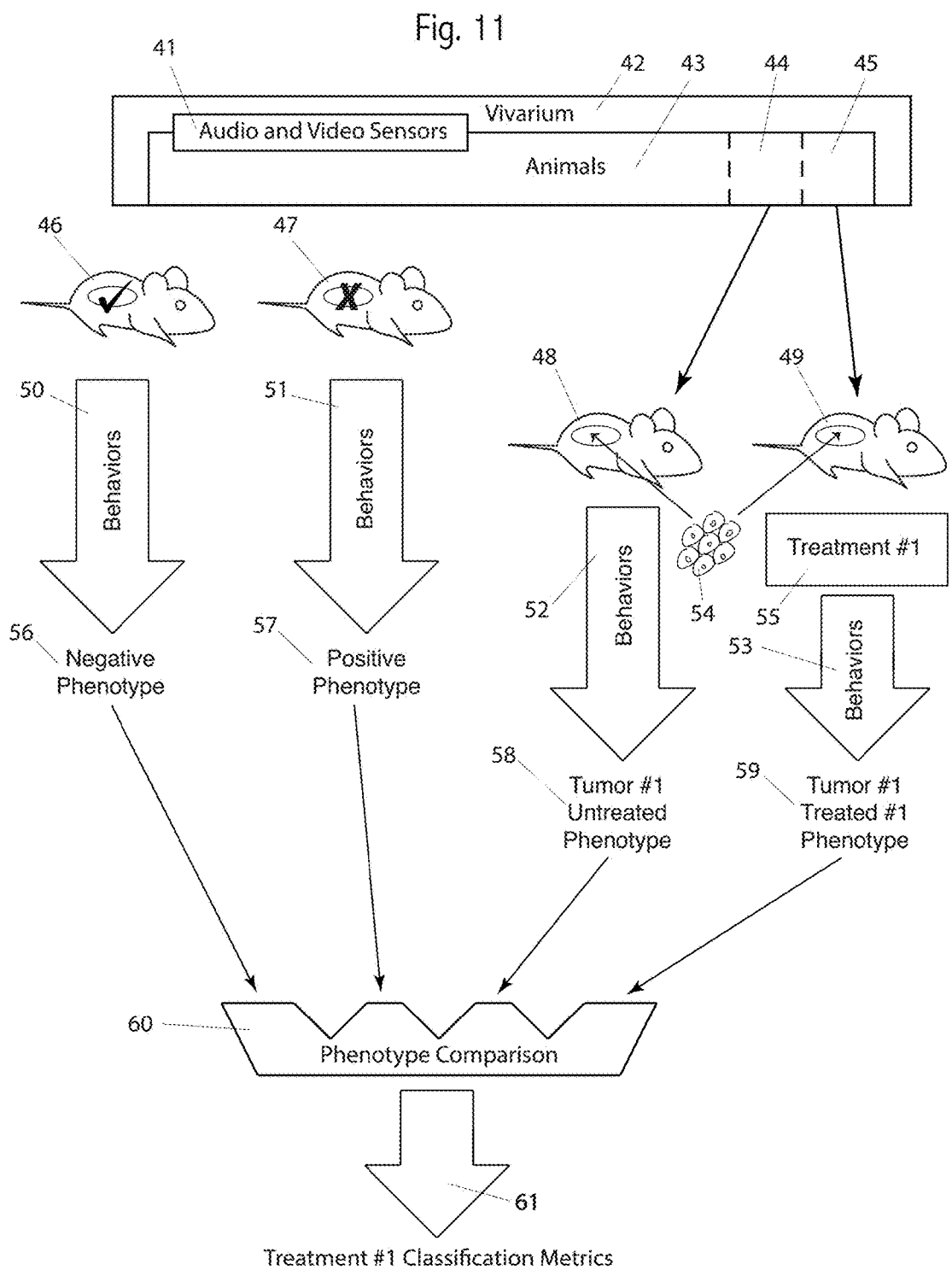
FIG. 11 A block diagram of a system and method of phenotype comparison for drug efficacy using both audio and video behaviors.

Turning now to FIG. 11, we see key elements of embodiments of both a system and method. 42 is one or more vivariums housing animals, 43, such as rodents such as mice, rats or guinea pigs; or rabbits, or livestock, or research animals, or pet animals, or even humans. In some embodiments the vivarium is an alternative and appropriate housing for such animals, such as a barn, farm, veterinary clinic, home or hospital. In some cases the animals may be wild. 41 shows sensors adapted to detect, observe, and communicate the behavior, physiology parameters, husbandry metrics, animal ID, and environmental conditions. Behaviors include both audio and video behaviors, as described elsewhere herein, as well has behaviors that are not detectable via audio or video, as weight gain, urine and blood chemistry, and the like. Storage, analysis, and communication of such information may be included in the sensors or separate. Suitable sensors measure cage, air and animal temperature, air and cage humidity, environmental light, animal weight, animal ID, such as barcodes or RFID, animal activity, including motion, exploration, parenting, fighting, nose pokes, exercise wheels, eating, drinking, urinating, defecating, cleaning themselves or other animals, burrowing, animal sounds and noises, ammonia in the cage or exhaust air, and $CO_2$ concentration. Sensors may include cameras, including still and video, color or monochrome, visible or infrared light. Sensors may include both ultrasonic and human-audio microphones. Some embodiments use auxiliary infrared lighting, or other light spectra to which the animals are not sensitive or are less sensitive. Some embodiments may use intermediate sensors or indicators, such as pH detecting chemicals in the bedding, or a wireless scale or wireless exercise wheel. Some embodiments use feedback, either positive or negative, to reinforce or discourage selected behaviors. Husbandry parameters may be measured, such as water, food, condition of bedding, and exercise. Social behaviors including fighting, mating and parenting may be observed and measured. Image analysis is often used to detect, differentiate, identify, quantify, store, compare and communicate the above or other behaviors or characteristics. The term behavior is typically broad, including internal and external behaviors and physiological parameters, such are urine and breath components, and vocalizations, unless specific narrowness of a behavior is stated, specifically claimed or indicated. All lists in this paragraph are non-exhaustive and non-limiting examples.

The sensors, 41, communicate directly or indirectly, via a network or other connections, wired, wireless, optical or audio, using digital or analog encoding, to a computer system, which may be local or remote, monolithic or distributed that performs the phenotype comparison, 60. Such communications are not shown in this Figure. The sensors may be located in one or more cages, or external to a cage. In one embodiment the cages are free of electronic penetrations, which assists in maintaining sterile cages and in vivarium management. Sensors may be per-cage or may monitor multiple cages.

The animals, 43, may be divided into groups or subgroups, which may be identified as sets or subsets. Two such subsets are shown as 44 and 45. Typically, the subsets, such as 44 and 45, use study-equivalent animals, such as identical mouse strains.

A key part of embodiments is observing, collecting, analyzing and comparing sets of behaviors, also called phenotypes, from different sets of animals. Such comparisons are used to generate quantitative assessment of treatment efficacy and classifications of animals, behaviors, treatments, drugs, and organs.

FIG. 11 shows four phenotypes, 56, 57, 58, and 59. Not all embodiments use all phenotypes. Two phenotypes, 56 and 57, may be thought of controls. Here, the negative phenotype, 56, represents healthy animals, ideally of the same or a compatible strain used for the treatment phenotype, 59. However, in some case an ideal phenotype for healthy animals that are medically identical is not available, and the next best phenotype may be used. The checkmark for animal 46 shows that the animal, or at least the organ or location of interest, the ellipse in the animal, is normal and healthy. A portion of the path, from animal 46 through behaviors 50 to the negative phenotype 56 may be part of embodiments or may be separate, such as behaviors or phenotypes known in the art, or measured earlier using the same or similar system, apparatus or method.

Note that the animals shown in FIGS. 11: 46, 47, 48 and 49, may be singular or plural (groups), although generally more than one animal to generate the phenotypes is preferred. For each shown animal the ellipse represents an organ, a location in an organ, or a location in the body. Organs include the brain, liver, stomach, colon, skin, glands, breast, prostate gland, lungs, heart and other organs. There are numerous locations in the brain that control specific functions of behaviors of the animal, which are well documented in the art. In addition, embodiments of this invention identify locations with more accuracy and specificity, and more behaviors and more accurate measurement of behaviors, than in the prior art. Locations not always considered as organs include bones, bone marrow, muscles, limbs, circulatory system and subcutaneous locations. In this Figure, a checkmark indicates healthy or untouched by the study (which is not always a healthy organ, as it may actually be compromised or missing). An X indicates not healthy, or functioning differently than the organ with the checkmark.

A positive control, the positive phenotype 57, is generated by the chain from animal 47 through behaviors 51, again known or observed behaviors, through to the phenotype 57. Note that the control phenotypes 56 and 57 are shown with animals 46 and 47 that are not from the animals, 43, in the vivarium, 42. These control phenotypes may be known in the art, or generated previously. Also note that each step in a chain, for example, 46 to 50 to 56, may occur at different times, or they may occur effectively in parallel. Most behaviors are not instantaneous, but rather occur over time, such as the amount of movement in a 24-hour period, or the amount of food consumed over the lifetime of the animal. However, some measurements such as ammonia in the exhaust air, cage temperature, or time of death, are effectively measurements at one point in time. Thus, "behavior," "behaviors," "sets of behavior," and "phenotype" usually comprise a mix of time-interval observations and instantaneous observations. Controls, both positive and negative controls, may be repeated in each study, or they be generated once, or they may not be generated in a particular study, as prior controls or other information in the art may be used.

We refer to "unhealthy functioning" or "unhealthy behavior" to identify functioning or behavior consistent with an organ or a location in an organ missing or damaged. For many organs, symptoms of disease of that organ are well known in the art. For the brain in particular, the large list of symptoms of brain tumors is reasonably matched to locations with the brain. For example, neurologic symptoms may include cognitive and behavior impairment, including impaired judgment, memory loss, lack of recognition, special orientation disorders, poor performance on object recognition, personality or emotional changes, hemiparesis, hypoesthesia, aphasia, ataxia, visual field impairment, impaired sense of smell, impaired hearing, facial paralysis, poor vision, dizziness, partial or full paralysis, hemiplegia, or impairment in swallowing. We do not provide a list of matching locations in the brain for the above partial list of symptoms, as this document is not for the purpose of medical diagnosis. The above list provides some examples of "unhealthy behavior." Unhealthy behavior may also be the behavior of one or more animals that have received an injection of tumor cells (neoplasm) but have not received any treatment. Unhealthy v. healthy behaviors may include vocalizations. For example, a vocalization for pain may be the only way to detect an animal in pain. Similarly, a vocalization that indicates confusion may be the best or only way to detect confusion in the animal.

Continuing with FIG. 11, a typical study involves testing one or more treatments, such as treatment #1, 55. Some uses and embodiments are also used for classifications, and thus may not require a treatment. For example, different strains of animals, such as different strains in subsets 44 and 45, may be observed for classification. Ideally, a treatment, 55, is compared for efficacy (and side effects, see FIG. 12) against one or more control groups. One such control is shown as the chain 44 to 48 to 52, and then to 58.

The treatment chain starts with a subset of animals 45, in which a tumor, neoplasm or other organ-compromising agent, 54, is injected into the animal 49, in the organ or location shown as the ellipse. Although injection, specifically, into a selected organ or location is core to one embodiment, other routes may be used, including oral; ear, eye or nose drops, and the like. Then the behaviors, 53, of animal 49 are automatically and electronically observed, starting with sensors 41. The aggregate of these behaviors, of treated animals 49, are the "Tumor #1, Treated #1 Phenotype" shown as 59. Note that, more completely, phenotype 59 also comprises data regarding the animals (e.g., strain) in subset 45, the neoplasm 54, the organ and location (ellipse in 49), and environmental conditions from sensors 41. Core advantages over the prior art, of continuous, electronic, automatic monitoring, via sensors 41, is the ability to detect new or more subtle behaviors; the ability to measure quantitatively behaviors that previously did not have repeatable quantitative numbers; and to observe and measure behaviors, physiological and environmental parameters beyond the reasonable observation ability of human observers, such as animal behavior in the dark.

The study control chain of subset 44, animal 48, behaviors 52, resulting in the "Tumor #1 Untreated Phenotype," 58 measures the behavior of animals with the same problem (e.g., tumor in a specific location in a specific organ) as the treated animals, however these animals are untreated.

Note that control group starting with animal 46, producing the negative phenotype, 56, may receive handling and environment similar to animals 48 and 49, but without the neoplasm 54. For example, these animals may receive a benign injection of saline in a gel, of the same volume as the neoplasm 54. Such a control group may be viewed as a "higher quality control" than a generic negative phenotype, 56. Note also that yet another control group, not shown in FIG. 11, is a control that is healthy, from a subset comparable to 45, that receives treatment #1, 55, but has not received the neoplasm, 54. Such a control group is useful for establishing the side effects of Treatment #1, 55, that are directly related to the treatment rather than from the neoplasm 54 or the interaction of the treatment 55 with the neoplasm 54 in an animal 49. Such a control group may be used for identifying a set of negative baseline behaviors.

One useful way to think about behavior observation, such as 50, 51, 52 and 53, as distinct from the phenotypes being analyzed, 56, 57, 58 and 59, but certainly not a limiting or exclusive way to think about any such differences, is that the behaviors represent data in a more raw form, while the phenotypes are the data in a form useful or compatible with numerical or statistical comparison performed in step 60. Such "raw" form of data may be completely unprocessed, such as a video stream, and audio stream, or a sequence of scale weights. Or the data may be partially processed, such as a smoothed curve of the animal's weight over the course of the study, or the results of audio pre-processing or vocalization word or phrase identification, or the results of video analysis providing movement metrics of specific animals in a cage. Or the data may be highly analyzed and reduced, such as a single growth rate metric, or a metric of minutes-per-day of animal movement, or a computed or inferred heart rate.

Continuing with FIG. 11, a key step is the analysis and particularly the comparison in step 60 of the multiple phenotypes 56, 57, 58, and 59, in any combination. It is important to note that in many embodiments not all four phenotypes will be used in the comparison. In particular, the two positive phenotypes 57 and 58 may be effectively so similar that only of the two is needed. Phenotype 57 represents "known" behaviors associated with functioning or malfunctioning of the organ and location shown by the X in animal 47. Phenotype 58 is a higher precision control group whose only meaningful difference from phenotype 59 is the missing treatment, 55. Animal studies are expensive. If existing phenotype 57 is adequate to represent phenotype 58, then it is economically advantageous to not generate phenotype 58.

Note than for many studies more than one treatment is provided to animals and measured in parallel. Thus, the path from 45 to 49 to 54 to 55 to 53 to 59, is often in parallel for numerous different treatments, 55. In this Figure, one such treatment, "Treatment #1" is shown.

Neoplasm 54 may be from a known tumor strain, or may be from a specific human or animal patient, or may be from another source. Neoplasm 54 may be replicated in vivo or in vitro, or not replicated. It may be partitioned in to smaller units so that multiple animals 48 and 49 may receive a portion of the neoplasm. One suitable range of cell counts for implantation in mice is $1\times10^5$ to $1\times10^6$ cells.

Continuing with FIG. 11, we consider the comparisons in system element and step 60. Before discussing the algorithms in 60, we first talk about what is compared. Although some embodiments deal with classifications, we first discuss a primary goal of embodiments: measuring the efficacy of various treatments, one treatment of which is shown as 55. In a perfect world, the treatment would cure the cancer 54 and the animals 49 would behave compatibly with animals 46. That is, phenotype 59 would be statistically indistinguishable from phenotype 56. We might score such a treatment as "zero," as its computational efficacy distance from phenotype 56. In nearly all cases (with considerations of side effects, cost, and the like) the closer the treatment that produces phenotype 59 is to phenotype 56, the better the treatment. Thus, an important comparison is phenotype 59 to phenotype 56. As mentioned previously, animals 46 may receive a benign injection at the checkmark.

Alternatively, a treatment, 55, of animals 49, that has no effect (except side effects, cost, and the like) would be statistically indistinguishable from phenotype 58. We might assign the computational or statistical difference of "zero" to such a completely ineffective treatment. As discussed above, phenotype 57 may substitute for (or be used in addition to) phenotype 58.

It might be more useful to think of a scale, say, from zero to 100, where a score of zero is the idealized perfect treatment whose resulting phenotype 59 matches phenotype 56, and a score of 100 is a completely ineffective treatment for this neoplasm 54 at its injection location, in which phenotype 59 is indistinguishable from phenotype 57 (or alternatively, phenotype 58). Note that this scale in not generally used in the art, but is useful for discussion purposes in this document.

Also, it is particularly important to note that such an artificial scale of zero to 100 is, by definition, in a single dimension. Although such single-dimension metrics of efficacy are common in the prior art, such as diameter of tumor size, or tumor growth rate, key embodiments provide multiple dimensions of efficacy, and may also provide aggregated metrics than combine metrics from more than one dimension. For example, liver failure is characterized by a wide range of physiological failures and behavioral changes. Treatments for liver cancer may not alter this range of failures and changes equally. In addition, one such treatment maybe most effective for early stage cancers (for example, by lowering the growth rate) while a different treatment is most effective for late stage cancers (for example, by minimizing the most undesirable side effects). As another example, many treatments generate undesirable side effects. A preferred treatment may be selected on the basis of its side effects. Thus, it is highly desirable to provide researchers, doctors, and sponsors with efficacy metrics along more than one dimension.

Key improvements over the prior art of embodiments are the ability to generate efficacy metrics in more than one dimension.

In practice, most usable treatments score neither zero nor 100, but in between. Thus, to generate a single metric (scalar) in a single dimension, it may be necessary to "weight" the two differences—59 to 58 and 59 to 56—including using all of only one or the other. Any combination of weights may be suitable, depending on the treatment, purpose, approved evaluation methods, prior evaluation methods, goals of the research or sponsor, and other factors. In general, if the treatment results, phenotype 59, are closer to phenotype 56, then that distance should be weight more. Similarly, if phenotype 59 is closer to either phenotype 58 or 57 that distance (or distances) should be weighted more.

Note again that ideally, efficacy comparisons, analysis and measurements and displayed results, 61, are ideally multi-dimensional, including such factors as side effects.

Staying with FIG. 11, we discuss methods of phenotype comparison in element or step 60. In general, statistical analysis is used. However, some analysis use numerical analysis is not universally regarded as the domain of statistics. The core tools of statistical analysis for data sets like those of the relevant embodiment are well known in the art, although some embodiments incorporate novel variations, implementations, improvements and applications. The software suite known as MATLAB®, from The MathWorks, Inc., Natick Mass., provides a well-known, extensive set of tools that may be configured and used in a wide array of combinations. There is no requirement to use any of these commercially available tools. This URL, as of the date of this document provides lists of both commercial and open source statistical software: https://en.wikipedia.org/wiki/List_of_statistical_packages.

Software tools and methodology for phenotype comparison, in element or step 60 include a non-limiting list of:
- principal component analysis,
- principal component regression,
- linear regression,
- time series analysis,
- Markov analysis and models, and
- clustering.

Other well-known steps that may be used to reduce and improve raw data, typically prior to statistical analysis include the non-limiting list of:
- smoothing,
- averaging,
- outlier elimination,
- slope determinations, such as least-squares-fit,
- known curve determinations (e.g., exponential growths), such as least-squares-fit, and
- decimation.

Clustering is particularly useful when analyzing large amounts of data in multiple dimensions. For example, the many known indicators of side effects may be clustered to identify common combinations. Then, treatments may be compared to find the nearest cluster to the particular combination of side effect behaviors observed from the treatment. Clustering algorithms are also good at creating a single metric, a "distance" in such a multi-dimensional space. Such a single metric is a useful summary or first-level characterization of a treatment or classification. As another example, the set of behaviors for phenotype 56 is in a multidimensional space, as evidenced by both the above list of possible attributes measurable by sensors 41 and the above list of behaviors. Each sensor's output and each namable behavior may be considered as one dimension, and time-related variations (such as activity level during the day compared to activity level at night) considered as additional dimensions. This large number of dimensions also applies the other phenotypes, such as 58. A clustering algorithm determines the "distance" in this multidimensional space between phenotypes 59 and 58, and again for the distance between phenotypes 59 and 56. These distances may then be used as "single dimensional" metrics, as described above. The clustering algorithm could also define a "scale" for this distance. For example, the distance from phenotype 56 to 57 or 56 to 58 might be given the value of 100. Then, distances are likely to have a value between zero and 100, inclusive. Of course, some treatments could make a problem worse, so treatment distances might exceed 100 in such a case.

Other statistical and numerical methods also produce results similar to the "distances" discussed in the above paragraph, and these distances may be used similarly.

Electronic observation, isolation, classification, quantification, analysis, communication and display of animal behaviors are critical steps in methods of embodiments as are the systems and devices that are used to perform such steps. We may generally divide data analysis of video behaviors into the following four groups:
  (a) Video image recognition to extract data that feeds the next step(s), such as animal location in a cage, animal identification, animal activity, biological indicators, etc.
  (b) Extracting quantitative behaviors from the above, such as sleeping/awake/eating cycles, time and quantity of movement, abnormal behavior such as a limp, tremor or fighting, patterns of normal behavior, such as burrowing, exploring, mating, nurturing and exercise.
  (c) Comparing data from the prior step(s) to baselines behaviors to provide some observable and meaningful, quantitative comparison. Baselines may be negative (healthy animals) or positive (animals with known tumors).
  (d) Displaying behavior differences in the form of graphs and other visual forms. This includes any final summary, such as numerical treatment effectiveness within a statistical probability.

Each of the above data analysis and presentation may be well known methods, and are outside of claimed embodiments. However, one or more novel methods may be used in one or more of the above steps and are claimed in the scope of one or more embodiments. Included in the claimed scope are graphs showing multiple behaviors, individual and combined metrics, of the various different phenotypes discussed herein, on timelines. Although we use the terms "video" and "image recognition," these are exemplary only, with no exclusion of other methods of acquiring data, such a RFID based motion sensing, exercise wheel activity sensing, one or more weight sensors, one or more motion sensors, thermal sensors, embedded sensors, solid state chemistry, molecular and cellular sensors, and the like.

For step (c) above, known analysis methods include multivariate analysis and clustering analysis.

As we discuss in more detail below, some embodiments skip step (b).

We may generally divide data analysis of audio behaviors into the following four groups:
  (a) Audio data collection and filtering. This may include not recording during quiet periods; separating audio data into frequency bands, particularly a human-hearable band; a lower frequency ultrasonic band, and a higher frequency ultrasonic band. Filtering may be frequency domain. Filtering may be optimized to minimize recording or amplitude of noise.
  (b) Identification, optionally with numerical weights, of audio words and phrases. This data analysis group may comprise applying weights to different audio word and phrase criteria, as described elsewhere herein.
  (c) Comparing data from prior step(s) to baseline behaviors to provide some meaningful, quantitative comparisons. Baselines may be negative (healthy animals) or positive (animals with known tumors).
  (d) Displaying behavior differences in the form of graphs and other visual forms. This includes any final summary, such as numerical treatment effectiveness within a statistical probability.

Baseline behaviors may be considered as one or more control groups. Such baseline behaviors may be negative, in that the behaviors are consistent with healthy animals, free of any known disease, tumor or treatment. Baseline behaviors may alternatively be positive, consistent with the behaviors of animals with a known disease or tumor in a particular organ or at a particular location in a particular organ.

Such baseline behaviors may be known in the art. While identifying and using such known baseline behavior data is part of some claimed methods, systems, and devices, generation of such baseline behavior data is not part of those claims.

On the other hand, generating one or more baseline behaviors is an important and novel part of some embodiments, particularly behaviors that include or combine audio behaviors. For usable baseline behaviors for effective comparison in a study, the behavior must be generated under same conditions using the same sensors, and the same analysis as the behavior of the non-control study animals. Thus, general classification in the prior art is insufficient to be used in such embodiments. Such specific, and often local to a single vivarium or animal type, behaviors or phenotypes may include the exact species and clonality of animals, the nature of the cages, temperature, cage environment such as temperature, lighting, and bedding, husbandry aspects such as food, water, handling and socialization. In some embodiments only a positive control is used. In some embodiments only a negative control is used.

Figure 12:
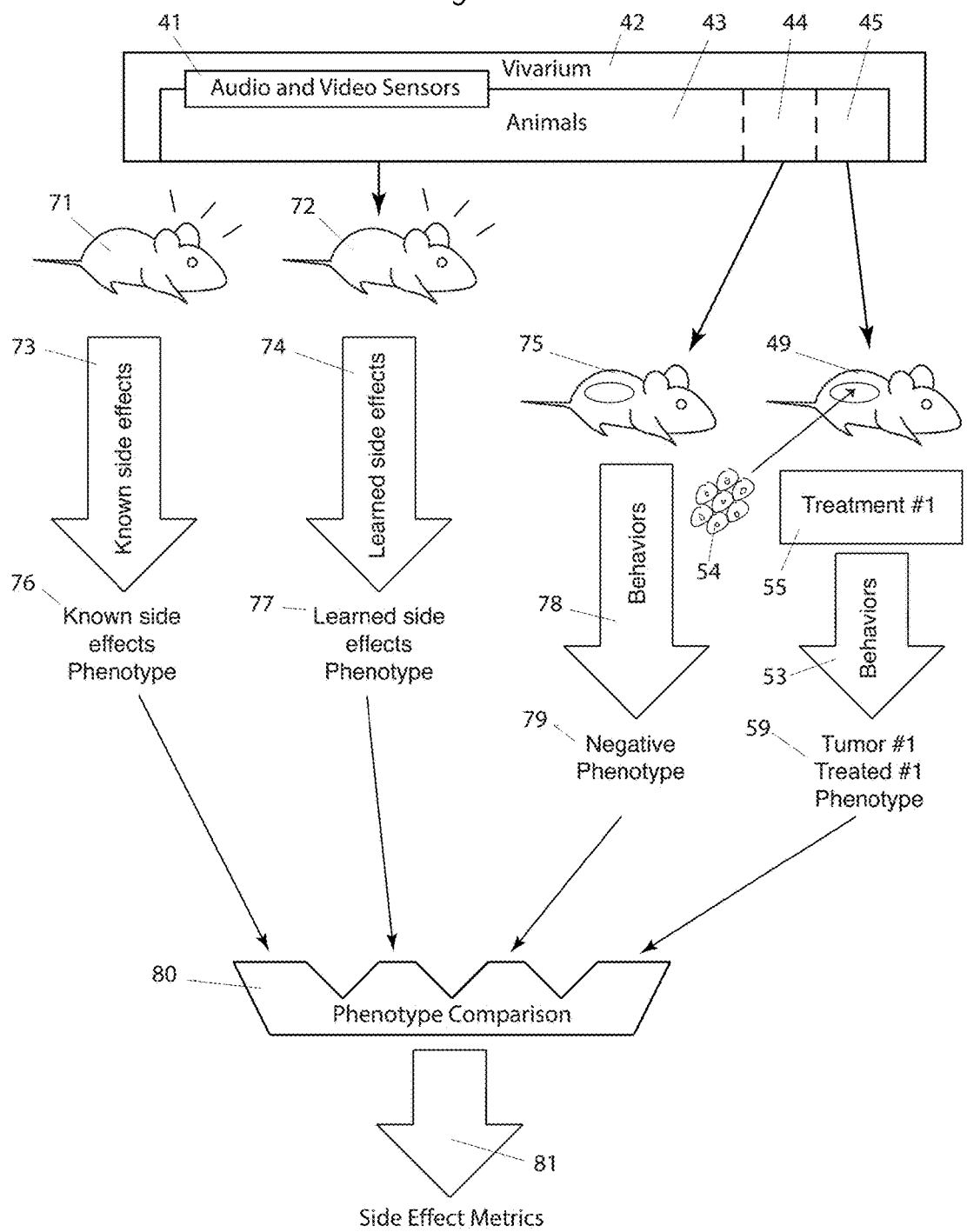
FIG. 12 A block diagram of a system and method of phenotype comparison for side effect measurement and classification using both audio and video behaviors.

Turning now to FIG. 12, we see one embodiment for use in analyzing comparing, evaluating, and quantitatively measuring side effects of various medical treatments. Unless otherwise stated, comments above apply to this Figure. Elements with the same reference designator as prior Figures are the same, equivalent, or functionally similar elements, unless otherwise stated or clear from the context. References to these duplicated reference designators will not generally be repeated below.

In FIG. 12, as in FIG. 11, embodiments observe the behaviors of animals 43 in a vivarium 42 (or other living environment suitable for research) using sensors 41. Such behaviors are aggregated as phenotypes and then statistically or numerically compared. A difference from FIG. 11 is that this Figure emphasizes comparisons to side effects and classifications thereof, rather than efficacy.

Control groups are shown as the chains 71 to 73 to 76 and 43 to 72 to 74 to 77. Both of these control groups measure side effects. The chain 71 to 73 to 76 produces phenotype 76 as a phenotype of known or previously measured side effects. The chain 43 to 72 to 74 to 77 produces a phenotype of currently or recently learned side effects from same core animal population as used for other elements of a study, such as for phenotypes 79 and 59, discussed below and above, respectively. The key difference between phenotypes 76 and 77 is that phenotype 76 represents information known in the art, or previously determined, compared to phenotype 77, generally determined as part of a current study. In general, phenotype 77 is likely to more accurately represent side effects relevant to the current study, due to the same or similar animals (e.g., mouse strain) and the use of similar or identical sensors, 41, and comparable phenotype generation and phenotypes 79 and 59. However, the use of known side effects, phenotype 76, is lower cost and may be faster. For analysis and comparison, such as performed in element or step 80, either or both phenotypes 76 or 77 may be used as the "positive" control group for side effects, although typically only one phenotype will be used.

Animals 71 and 72 are depicted as not feeling well. A major, novel advantage and benefit of embodiments is that continuous, automatic behavior observations are able to detect new and subtle behaviors that may more accurately mimic human side effects than prior art observations and measurement. This is particularly true for audio behaviors or combined audio and video behaviors. In addition, behaviors that are not readily observed by human observers, such as animal behavior in the dark, or ultrasonic audio vocalizations, may also be electronically observed and analyzed. In addition, behaviors aggregated, categorized, or processed into phenotypes are generally far more quantitative and repeatable than prior art human observations and measurements.

The chain 45 to 49 to 54 to 55 to 53 to 59 is the same or similar to discussions above regarding this chain. This is a treatment chain, where a goal of embodiments is to measure and compare side effects of this chain.

Unique to FIG. 12, compared to FIG. 11, is that steps 54 or 55 are optional. If the goal is measure side effects solely from the implantation of neoplasm 54 (and variations as discussed above), then no treatment 55 is necessary. More likely, step 54 will be skipped so that side effects solely from the treatment 55 may be measured and classified.

Typically, phenotype 59, possibly without step 54, is compared to either phenotype 76 or 77.

The algorithms, statistics and numerical analysis in element or step 80 are similar to element or step 60 in FIG. 11, and those extensive comments and explanations are not repeated here. The results of element or step 80 are the comparison metrics, in one or dimensions, 81. These metrics have corresponding comments and explanations as element or step 61 in FIG. 11 and will not be repeated here. The multidimensional aspects of side effects lend themselves particularly to multidimensional analysis, as compared to metrics in a single dimension, as discussed above.

In addition, side effect phenotypes 77 may also be compared to organ failure or dysfunction, such as phenotype 57 in FIG. 11.

In FIG. 13 we see an exemplary chart showing core elements of a particular study plan. Typically, much more information and planning are required in practice. The top chart shows animals requested for the study. The Strain column indicates an industry name for a strain, or a model number from a particular vendor. The Category defines either an industry description or a vendor description to further identify desired animals. The Qty column is the number of animals that will be used in the study. The Age column shows the age of the animals at the start of the study. The Gender column describes the gender of the animals that will be used in the study. The Weight column is blank because that may be filled in later, for example when more information is known, or actual animals are ordered or received for the study. The optional Description field permits additional notes or animal description, which may be filled in when animals are actually ordered or received.

The second table in FIG. 13 shows a plan for treatment groups. Here 11 treatment groups are planned, one shown per line. The first column, ID may be the study number, here "1" for all treatments. Alternatively, this column may be used to numerically identify a treatment group. Each treatment group has a Treatment Group Name, shown in column 2. The Treatment Group Name may be shorthand for an injection site, planned treatment, type of control group, or other. The Qty column shows the number of animals for each treatment group. Note that the 5 animals each in 11 treatments matches the 55 animals requested in the top table. The Test Material column shows, typically, the identification of the material to be injected and the quantity, if applicable. The material to be injected may be a standard neoplasm identifier or may be specific to one source, one study, or one patient. The number provided is a cell count, such as $1*10^5$, or 100,000 cells. In some cases, based on the route or for other reasons, the cell count may not be provided, or it may be filled in later. The fifth column, Dose Volume and Route identifies the particular location, organ, or location in an organ for the injection, or other route of delivery. A volume may be appropriate for some injections, particularly placebo injections or cells in a gel or suspension. Also, coordinates for stereotaxic injection may be provided in this column. The Notes column is for any desired additional information about the treatment on that line. The last column, Animal IDs, will be filled in when the specific IDs of the animals for that treatment are known. As discussed elsewhere herein, multiple methods of animal ID may be used, such as RFID, tattooed barcodes, and the like.

The table in FIG. 14 shows an exemplary, partial, procedure schedule. For the Day column, a reference day number is selected. Here, day 0 is the day of injection. Prior to that day, such as shown in the top table line, row "−7," days may be used to establish baselines, particularly negative baseline behaviors. At Day 0, shown on the second line, a task is shown for injection of identified neoplastic cells. Line three shows that days 0 through 49 will be used for continuous behavior monitoring, as described elsewhere herein. The last row, "Terminal endpoint," identifies the actions for the end of the study or treatment. Terminal endpoints may occur prior to the last date planned for observation, for various ethical and practical reasons, such as poor animal health. The Date column shows the date that will be filled in later in the planning process or when that line is actually executed. The Task column and Description column provide the necessary information to summarize the necessary steps for the procedure. Examples for "Description" include, but are not limited to, weight, respiration, activity levels, and circadian activity. The last column, "Assigned To," will be filled when the task is assigned to one or more personnel. Note that although behavior collecting, measuring and timing is automatic, personnel are needed to start and verify that the automatic processes are working properly. Such personnel do not manually observe animal behavior nor make manual entries regarding human observed behaviors. Euthanasia and post study analysis may be manual. Columns not shown in FIGS. 13 and 14 include cage number, rack number, sponsor name, and other information needed in practice.

The exemplary data shown in FIGS. 13 and 14 may be on paper, in a spreadsheet, or in a database, or in another useful format and medium.

An organ of particular interest, used in some embodiments, is the brain. A region of the brain of particular interest, used in some embodiments, is the cortex.

One range of suitable cell count for injection is $1*10^5$ to $3*10^5$ cells. Another suitable range of cell count for injection is $1*10^4$ to $1*10^6$. Yet another suitable range of cell count for injection is $1*10^3$ to $3*10^6$. A suitable range of injection volume is 2 μl to 10 μl. A suitable range for injection times is 2 to 10 minutes. These ranges apply to studies using mice. A suitable strain of mice for studies of brain tumors is C57BL/6, or an immunosuppressed model that accepts human cells, such as NSG mouse model from Jackson Labs. A suitable method of intracranial implantation of cells is via stereotaxic equipment and methods. All information in this paragraph is specifically claimed and may be added or used to modify any portion of any other claim.

In some embodiment a histological examination is performed.

Repeatable results are of particular importance. In some embodiments, ranking, approval, selection, classification, or any combination, is responsive to repeatability. Such filtering of data, behaviors, results, efficacy or suitability for further studies or treatment, responsive to repeatability of results; is specifically claimed. Repeating any combination of steps in methods or using a system or parts of a system repeatedly in order to establish a level of repeatability is specifically claimed.

Uniform tumor growth in all study animals in a study is important. Histological examinations, assays, direct or indirect measurements of tumor size, as part of claimed systems and steps in claimed methods are specifically claimed. In particular, such examinations, assays, and measurements, used for the purpose of calibrating, providing numerical relationships, or validating the use of behavior to determine the extent of a tumor or disease, or the quantitative determination of efficacy of a treatment or classification of behavior, is specifically claimed for both systems and methods.

A critical, unique and novel aspect of systems, devices and methods includes the automated, continuous monitoring of animals' behavior through the use of electronic cameras, ultrasonic microphones and other communicating electronic sensors proximal to each cage. Such detailed, comprehensive, and continuous monitoring will often allow subtle behaviors and a wider scope of behaviors to be detected and quantified that existed in prior art. Such a substantial increase in the quantity, quality and scope of behavioral data is beyond prior art in many more ways than simply quantity or automation. Drugs and other proposed treatments may be tested at speeds and in combinations that were not possible in the prior art. As one example, personalized treatments for individual patients' specific tumors may now be developed and tested in animals fast enough to use to treat a human patient before the patient dies. Prior art could not develop or test treatments with sufficient timeliness for this type of personalized medicine.

The fundamental nature of animal studies of proposed drugs or other treatments for tumors and other diseases is the extent to which the treatment moves the patient closer to a negative control or farther from a positive control. For tumors, the negative control is no tumor, or a tumor that does not grow. The positive control is the growth rate of a tumor of the same neoplastic type in the same location that is not treated. In the prior art, the size of the tumor was measured directly, as described above in the Summary. A nexus of embodiments of this invention is using observed and analyzed behaviors to produce a measurement of the difference between the results of the treatment under study and the negative or positive controls. We refer to both negative and positive controls as "baseline behaviors."

For brain tumors, there exists in the prior art "brain maps," which show which three-dimensional locations in the brain correspond to what body functions, which in turn drive detectable behaviors. For example, the motor cortex controls movement. Damage to the motor cortex may generate abnormal movement, such as a limp or a tremor, or a decrease or increase in overall movement. With further damage, paralysis may result: both breathing and movement will be abnormal. Thus, a variety of behaviors are associated with a particular brain location, and in addition, those behaviors also identify a level of damage to that region. In this way, careful, quantitative analysis of comprehensive behavior sets may be used, in some embodiments, to determine the extent or size of a tumor without having to measure the size of the tumor directly.

Of note is that the prior art of behavior observation was manual, and the behaviors had to be named and described, such as "walks with a limp," or "has a tremor in a forelimb," or "fails to perform parenting functions." However, in some embodiments behaviors do not need to be identified along such previously named categories. Data such as movement data, or association with other animals in the cage may be use directly to establish distance from baseline behaviors. For example, movement at one spectrum of frequency may be consistent with healthy animals (negative baseline) while a particular deviation from this frequency spectrum, such as faster limb movement (e.g. a tremor) or less movement in the cage (e.g. partial paralysis) may be numerical behavior suitable for use in treatment efficacy analysis without going through a particular naming step. The equivalent of "less parenting activity" may be less time spent near to offspring.

Many such numerical significant behaviors will not correspond to already recognized and named behaviors, whether normal or abnormal.

Thus, one of the novel benefits of continuous monitoring and analysis of animal behavior is detection of valuable behaviors that have not been previously identified (i.e., named).

Another advantage of continuous monitoring and analysis of animal behavior is the ability to quantify behavior that could not previously be quantified with non-continuous observation. For example, the frequency with which an animal drinks can only be measured quantifiably with continuous observation. As a second example, certain compulsive behaviors, such as walking in the same path over an over, rather than moving through a cage randomly, requires both continuous observation and automated motion analysis. Since treating compulsive behaviors (such as addiction and obsessive-compulsive disorder) in humans is a large and important part of modern medicine, the ability to detect compulsive behavior in animals is a new and novel benefit of embodiments.

Yet another advantage of continuous electronic monitoring is the ability to observe the study animals in a more natural environment, such as in the dark, under cover of bedding, or at a more natural temperature. (Previously, the formal recommended temperature range for vivariums was for the comfort of the human workers, placing the study animals at an unnatural temperature.) By using more natural environments for the animals, only possible with fully electronic observing, more accurate baseline behavior may be determined and more subtle changes from natural baseline behavior may be observed. This results in increased sensitivity and more accuracy in treatment results, which are benefits beyond the expected benefit of automation.

In some embodiments, there is no intermediate step of "identifying named behaviors." Instead, sensor data is statistically processed directly to produce a numerical distance between the treatment animals and the baseline animals. Such a result might be thought of as, "we don't know precisely in what ways the treatment animals are acting more like healthy animals than sick animals, but they are, and this treatment thereby has a determinable and repeatable efficacy." Of course, further analysis could identify some namable behaviors, such as, "the treatment animals explore their cages more." However, the results of the directly processed sensor data provide an earlier measure of treatment efficacy, and may also provide a quantitative efficacy that has a higher probability of correctness than one that relies exclusively on quantifying named behaviors.

Let us now discuss the sets of baseline behaviors in more detail. A "negative baseline" is the set of behaviors of healthy animals. (They are "negative" because they are free of disease.) A "positive baseline" is a set of behaviors consistent with a known location in a known organ. More generally, the positive baseline is a series of sets of behaviors, where the series starts with less sick and moves towards more sick. For example, let us consider five sets in five-step series. For convenience, we will name and number these as N0=healthy; N1=mildly sick; N2=moderately sick; N3=very sick; and N4=death by a known cause. In all cases the behaviors (which may also be thought of as symptoms, at least for a human patient) are consistent with a particular location in a particular organ. For example, consider the location and organ to be the motor cortex in the brain. Although N0 is the negative baseline, that is, behaviors of healthy animals free from any brain tumor, the behaviors of N1, N2, and N3, and the cause of death in N4 are all known to be associated with the functioning or failure of function of the motor cortex. N1 might include tremors. N3 might include partial or complete paralysis.

In a very simplified view, we may think of a path from N0 through N1, then to N2, and then to N3, ending at N4. This path represents the progress of a tumor at the known location in the known organ. Behaviors of an animal are analyzed to see which of the five Nx points they are closest to. More generally, the numerical analysis will seek to determine to which point on the N0 . . . N4 line the observed behavior is closest to, rather than specific points on the line.

Note that such a series in not necessarily quantized sets. That is, the path from N0 to N4 may be described by equations or statistics, not as five discreet sets.

In our above, simplified discussion of N0 through N4, we have talked about a "line." However, we are recording, aggregating, and processing a large amount of data from multiple sensors and many different types of activity from the camera images. Thus, our behavioral space has many axes, also called dimensions. The sets N0, N1, N2, N3, and N4 are actually statistical clouds within this multi-dimensional space. The path from the N0 cloud to the N4 cloud may be thought of visually as a 'snake', with its healthy head at N0 and its deadly tail at N4. The thickness of the body of the 'snake' at any point represents the statistical diameter of compatible behaviors for a certain level of sickness. In one example, the level of sickness may be correlated with the size of a tumor. In another example, the distance from N0 may be correlated with the days since an animal was injected with a known quantity of neoplastic cells. In yet another example, the distance from N4 may be days prior to death. The body of the 'snake' travels through our multidimensional space, not necessarily in a "straight" line.

In trying to determine the health of an animal with a growing tumor at a known location in a known organ, we want to determine where in the 'snake', between the N0 head and the N4 tail, the animal is most statistically likely to be. Numerous numerical and statistical techniques have been developed to answer this question, including clustering and multivariate analysis. In clustering analysis, we first create defined clusters for N0 through N4. Then we compute a distance from the measured behaviors of a subject animal and compute the distance to each of the N0 through N4 clusters.

When discussion quantitative behaviors for any group, including control groups, we specifically claim quantifying behaviors in one dimension, in two dimensions, in more than two dimensions, and also explicitly claim quantifying behaviors where the number of dimensions is not known or not clearly stated. The statistical and numerical analysis used, including the exemplary methods herein, may generate meaningful quantitative results by analyzing large amounts of data but without identifying any one or more distinct behaviors or metric axes. This is a significant departure from and improvement on prior art. Such prior art focuses on single metrics, such as tumor diameter, weight loss, body temperature, days before or after an event, and the like.

For some organs, such as the brain, detailed maps have been created that associated each part of the brain with particular body functions and certain behaviors. For many other organs, the location in the organ makes little or no difference. For example, cancers of lung, liver, kidney, stomach and colon typically produce known disease progress that is not highly sensitive to the location in the organ. Note that in some cases the source of neoplastic source in one location in an organ compared to another location in the same organ may influence the likelihood of one type of neoplasm or another type of neoplasm. For example, one type may grow faster, or may be more likely to metastasize, or may be more likely to cause death within a set time. However, as the organ fails, the sets of behaviors are consistent. That is, animals with different types of neoplasms may get sicker and die sooner, but the "path through the snake" is the same.

When we refer to "distance from the negative baseline set of behaviors," we are referring, in some embodiments, to the distance from N0 along the path of the 'snake' in our multidimensional space. When we refer to "distance from the positive baseline set of behaviors" we are referring to the distance from N4, along the path of the 'snake', in our multidimensional space. Note that in most cases "distance" includes either an implicit or explicit statistical probability or likelihood.

Thus, for some organs, the "location in the organ" is of less or no concern. Such a location may be in fact, "any location." Or it maybe simply, "a central location" in the organ.

Because most behaviors are inherently multi-dimensional, the term "set of behaviors" may be stated more compactly as "behaviors" or even "behavior." In our embodiments, all behaviors are quantitative, comprising some combination of metrics or some number of measured or measurable parameters.

Embodiments are specifically claimed for methods comprising any combination of steps shown in a Figure. Embodiments are specifically claimed for methods comprising any combination of steps shown in a Figure using an apparatus of one or more claims.

Definitions

Behavior and phenotype are two terms that may often be used interchangeably. Sometimes, "phenotype" refers typically to an aggregate of individually identified behaviors. However, phenotype may be singular, such as single animal type designation. Also, the term "behavior" (in the singular) may be used to describe a set, which may be a large set, of individual behaviors.

Behavior is to be construed broadly, including animal variable attributes as blood chemistry, composition of urine, heart and respiration, weight, and the like. Attributes that that an animal cannot readily alter, such as species type, genetic makeup, gender, age, and the like, may be included in a phenotype, or, considered as part of an "environment." Husbandry attributes, such as food, bedding, temperature, exercise equipment, cage mate, and the like are typically considered as part of environment. There is no bright-line boundary between behavior, phenotype, and environment.

Behavioral "phrases" consist of a sequence or group of behavioral "words." For example, a phrase, "grooming" might comprise a set of individual words such as licking, smelling, or inspection. A phrase, "fighting" might comprise a word sequence including approach, threat, biting, scratching, attacking, defense, or resolution. Similarly, a phrase, "mating" might comprise a specific sequence of behavior words.

"Animal cognition"—is an identifiable attribute, action, behavior or state of an animal that is in response to a stimulus or environmental condition that suggests a level of recognition by the animal.

"Animal emotion"—is an identifiable attribute, action, condition, behavior or state of an animal that corresponds to an emotion recognized in the art as an available emotion of a mammal.

"Audio" includes both ultrasonic frequencies as well as human-audible frequencies. Audio includes non-melodic sounds such as clicks, wheezes, sneezes, scratching, audible chewing, and the like.

"Audio behavior"—any behavior that is identified or identifiable using audio data of an animal, including both ultrasonic and human-audible.

"A first neoplasm type"—associated with a first tumor type or neoplasm type or categorization of tumor.

"First patient"—typically a human patient, although not necessarily human.

"Classification of a behavior"—is typically but not exclusively the process of accepting input and then outputting responsive to that input a behavior that has not previously been identified or well characterized by the input.

"Communication"—may be electromagnetic, optical or audio. Audio comprises sub-audio and ultrasonic audio.

"Computer"—may be local, distributed, in the cloud, mobile, or any combination. May be one or more computers, or a system of computers. References to electronic memory specifically mean, "non-transitory memory."

"Continuous collection of data"—continuous means repeated substantially without unnecessary gaps in collection time intervals, subject to the inherent limitations of the sensors, communications and data recording capability of the system or method; and the nature of the data collected. This "continuous" may be compared against manual data observation which might be performed hourly or daily, for example, but which could be observed more frequently if sufficient personnel were available to perform the observations. Such continuous collection of data may, in some embodiments, also occur during environmental times where manual observation is difficult, such as in darkness.

"Electromagnetic radiation"—may be visible or IR light, for example, imaged by a still or video camera. May be digital or analog radio signals, such as used by RFID, Bluetooth, WiFi, or other standard or proprietary communications. May be analog or digital optical communications.

"Home Cage"—The home cage is the cage is which the animal lives. It is different from special purpose, behavioral-measurement, behavioral-detection, or behavioral-observation cages that are generally used for only a short time for the duration of a particular test due to cost and mindset.

"Identification of a behavior"—is typically but not exclusively the process of accepting input and then outputting responsive to that input one or more predetermined behaviors.

"Innate behavior"—is a behavior of an animal that does not need to first be learned.

"IR LED"—any LED that is capable without limitation, by its radiation, of causing an animal within its directed radiation to increase in body temperature, that is, skin temperature or internal temperature, by an amount detectable by the animal, as observable. Note that the spectrum of the IR LED may or not be predominantly in the infrared with respect to the visible spectrum. IR LEDs may be used to increase sensitivity of video or still image cameras, or to increase contrast or other sensitivity to animal fur or skin. Note that "thermal" cameras are normally sensitive to spectra at much longer wavelengths that traditional "IR." However, in some cases, the term IR may be used to indicate thermal imaging.

"Normal living temperature"—a temperature range suitable for an animal to live normally or a temperature range appropriate for specific animal study. This may be Ta plus or minus a predetermined range, or an industry accepted range for use of the applicable laboratory animals in the applicable study.

"Pathogen-free"—means the population of microbes, including but not limited to bacteria, viruses, prions and toxins, relevant to the experiment, are sufficiently reduced to meet the needs of the study, or to not impact the health, performance or behavior of the target animal population or of the workers.

"Primary cage"—the cage in which an animal spends more time than any other cage. Of note, there is a related term of art: "home cage." The definition of primary cage is, in some embodiments, the home cage. An aspect of home cage/primary cage deals with the fungibility of the actual cage itself. Each time a cage is changed, the physical cage is generally either disposed or removed for washing, and replaced by a clean cage. The new physical cage is considered the same primary cage. A primary cage may sometimes be distinguished from a non-primary cage by the purpose of the cage. For example, a home cage may be for living in, as compared to an experimental cage to which the animal is transferred that is equipped or located for one or more particular experiments for the applicable study.

"Quantity of tumor cells"—any measured or measurable quantity of a source tumor or related tissue, cells, or tumor-related chemicals, such as a carcinogen. Such quantities or counts may be computed or inferred.

"Regimen"—is defined broadly to include any combination of treatments. A regimen may match one of the treatments, after adjusting for differences between the test subjects and the patient(s). However, one or more selected regimen may include combinations of treatments not tested directly, or different doses or different routes or different timing, or the use of similar drugs to those tested. A regiment may include treatment elements not tested in the study. What is important in selecting a regimen is that the selection is responsive to the phenotypes and differences between the phenotypes; that is, responsive to the steps in the method. The steps of the claimed methods or the use of claimed devices or systems informed the selection of a regimen.

"Sealed enclosure"—an enclosure that limits against entrance or exit of pathogens that impact or alter study results, or alter the credibility or repeatability of study results. The enclosure may not be sealed in the hermetic sense.

"Sensor"—may or may not include the use of local or remote processors, and may or may not include local or remote software executing on the local or remote processors. Sensors may or may not communicate over a network. Multiple sensors may or may not include common elements.

"Set and subset"—one or more, unless stated otherwise. A subset may include the entire set of which it is a subset, unless stated otherwise. When a first subset and a second (or third) subset are identified, these subsets are assumed to not be identical, although they may overlap, unless stated otherwise. In some embodiments, the different subsets have no overlapped members.

"Sterile"—pathogen-free for the purposes of the study. The exact level of sterility and the exact pathogens depends on the study and animals used. In some cases, sterile means, "free of undesirable pathogens."

"Treatment drug"—may also be a control, such as saline. Drugs may be administered via multiple routes. That is, treatment may also be "no treatment," or "benign treatment," such as might be used to establish a baseline, positive, or negative control group, data or sample.

"Ultrasonic" includes frequencies above 14 KHz but does not exclude frequencies that may be heard by a human.

"Video behavior"—any behavior that is identified or identifiable using video data of an animal.

"Visible light"—Free of visible light means the ambient light is sufficiently low and in a spectrum such that the animal's physiological state and behavior are consistent with its natural physiological state and behavior at night.

"Vocalization" or "audio behavior"—any behavior that is identified or identifiable using audio data of an animal. Note that some audio behaviors are not vocalizations.

"Xenograft"—used herein to mean its medical definition, roughly tissue outside of its normal or original location or species of origin. It is not necessary, in the definition we use, that the xenograft is from another species. The xenograft could be a tissue sample where the source, (e.g., a patient) is a different animal that the one receiving the xenograft. Also note that in many cases the tissue source of sample is "amplified" before use. A common method of amplification is growth in vivo or in vitro. This amplification may happen multiple times before the tissue sample (our "xenograft") is used in studies for embodiments herein.

Ideal, Ideally, Optimum and Preferred—Use of the words, "ideal," "ideally," "optimum," "optimum," "should" and "preferred," when used in the context of describing this invention, refer specifically a best mode for one or more embodiments for one or more applications of this invention. Such best modes are non-limiting, and may not be the best mode for all embodiments, applications, or implementation technologies, as one trained in the art will appreciate.

All examples are sample embodiments. In particular, the phrase "invention" should be interpreted under all conditions to mean, "an embodiment of this invention." Examples, scenarios, and drawings are non-limiting. The only limitations of this invention are in the claims.

May, Could, Option, Mode, Alternative and Feature—Use of the words, "may," "could," "option," "optional," "mode," "alternative," "typical," "ideal," and "feature," when used in the context of describing this invention, refer specifically to various embodiments of this invention. Described benefits refer only to those embodiments that provide that benefit. All descriptions herein are non-limiting, as one trained in the art appreciates.

Embodiments of this invention explicitly include all combinations and sub-combinations of all features, elements and limitation of all claims. Embodiments of this invention explicitly include all combinations and sub-combinations of all features, elements, examples, embodiments, tables, values, ranges, and drawings in the specification and drawings. Embodiments of this invention explicitly include devices and systems to implement any combination of the methods described in the claims, specification and drawings.

We claim:

1. A device for multi-dimensional classification of animal vocalizations comprising:
   a study animal type, wherein the study animal type is non-human;
   a vivarium comprising a set of study animals, of the study animal type, in a plurality of study cages;
   a set of environmental attributes consistent with the plurality of study cages;
   at least one ultrasonic audio sensor proximal to the each study cage of the plurality of study cages, adapted to receive, from the each study cage, audio vocalizations from at least one study animal of the set of study animals within the each of the study cage, and then communicate the audio vocalizations to a multi-dimensional processor;

at least one phenotype sensor proximal to each study cage of the plurality of study cages, adapted to detect and communicate one or more phenotype attributes of an animal in the each study cage;

the multi-dimensional processor adapted to accept as an input (i) the audio vocalizations, (ii) the phenotype attributes, and (iii) the set of environmental attributes, from the each of the at least one study animal;

wherein an output of the multi-dimensional processor comprises a set of multi-dimensional clusters responsive to the (i), (ii), and (iii) inputs;

wherein each multi-dimensional cluster in the set of multi-dimensional clusters is associated with an animal type, innate animal attribute, phenotype, or environmental attributes of the at least one study animal of the set of study animals within the each of the study cage.

2. The device of claim 1, wherein:

the each study cage of the plurality of study cages is a home cage of a respective animal, and free of electronic penetrations.

3. The device of claim 1, wherein:

the at least one ultrasonic acoustic sensor and the at least one phenotype sensor are mechanically independent of the each of the study cage such that the ultrasonic acoustic and the at least one phenotype sensors of the each of the study cage are replaceable without mechanically removing the each of the study cage or the ultrasonic and the at least one phenotype sensors, respectively; and wherein the set of environmental attributes is predetermined.

4. The device of claim 1, wherein:

the device is free of manually observed behavior of the set of study animals, and free of manually communicated behavior of the set of study animals, and free of manual classifying behaviors.

5. The device of claim 1, wherein:

the communication of the audio vocalizations and the detection and communication of the phenotype attributes are continuous.

6. The device of claim 1, wherein:

at least some study cages of the plurality of study cages comprise two or more animals of the set of study animals.

7. A method of classification of animal vocalizations using a device comprising:

a study animal type, wherein the study animal type is non-human;

a vivarium comprising a set of study animals, of the study animal type, in a plurality of study cages;

a set of environmental attributes consistent with the plurality of study cages;

at least one ultrasonic audio sensor proximal to the each study cage of the plurality of study cages, adapted to receive, from the each study cage, audio vocalizations from at least one study animal of the set of study animals within the each of the study cage, and then communicate the audio vocalizations to a multi-dimensional processor;

at least one phenotype sensor proximal to each study cage of the plurality of study cages, adapted to detect and communicate one or more phenotype attributes of an animal in the each study cage;

the multi-dimensional processor adapted to accept as an input (i) the audio vocalizations, (ii) the phenotype attributes, and (iii) the set of environmental attributes, from the each of the at least one study animal;

wherein an output of the multi-dimensional processor comprises a set of multi-dimensional clusters responsive to the (i), (ii), and (iii) inputs;

wherein each multi-dimensional cluster in the set of multi-dimensional clusters is associated with an animal type, innate animal attribute, phenotype, or environmental attributes of the at least one study animal of the set of study animals within the each of the study cage.

8. A system of classification of animal vocalizations using a device comprising:

a study animal type, wherein the study animal type is non-human;

a vivarium comprising a set of study animals, of the study animal type, in a plurality of study cages;

a set of environmental attributes consistent with the plurality of study cages;

at least one ultrasonic audio sensor proximal to the each study cage of the plurality of study cages, adapted to receive, from the each study cage, audio vocalizations from at least one study animal of the set of study animals within the each of the study cage, and then communicate the audio vocalizations to a multi-dimensional processor;

at least one phenotype sensor proximal to each study cage of the plurality of study cages, adapted to detect and communicate one or more phenotype attributes of an animal in the each study cage;

the multi-dimensional processor adapted to accept as an input (i) the audio vocalizations, (ii) the phenotype attributes, and (iii) the set of environmental attributes, from the each of the at least one study animal;

wherein an output of the multi-dimensional processor comprises a set of multi-dimensional clusters responsive to the (i), (ii), and (iii) inputs;

wherein each multi-dimensional cluster in the set of multi-dimensional clusters is associated with an animal type, innate animal attribute, phenotype, or environmental attributes of the at least one study animal of the set of study animals within the each of the study cage.

* * * * *